(12) United States Patent
Weindruch et al.

(10) Patent No.: US 6,569,624 B1
(45) Date of Patent: May 27, 2003

(54) IDENTIFICATION OF GENETIC MARKERS OF BIOLOGICAL AGE AND METABOLISM

(75) Inventors: Richard H. Weindruch, Madison, WI (US); Tomas A. Prolla, Madison, WI (US); Cheol-Koo Lee, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/630,567

(22) Filed: Aug. 8, 2000

Related U.S. Application Data

(60) Provisional application No. 60/148,540, filed on Aug. 12, 1999, provisional application No. 60/178,232, filed on Jan. 26, 2000, and provisional application No. 60/211,923, filed on Jun. 16, 2000.

(51) Int. Cl.⁷ .......................... C12Q 1/68; C07H 21/04
(52) U.S. Cl. ........................................ 435/6; 536/24.3
(58) Field of Search ............................ 435/6; 536/24.3

(56) References Cited

U.S. PATENT DOCUMENTS 6,087,102 A * 7/2000 Chenchik et al. ............... 435/6
6,406,853 B1    6/2002 Spindler

FOREIGN PATENT DOCUMENTS

WO    WO 96/13610    9/1996

OTHER PUBLICATIONS

B. Chatterjee, et al., "Differential Regulation of the Messenger RNA for Three Major Senescence Marker Proteins in Male Rat Liver," *J. Biol. Chem.* 256 (12):5939–5941, 1981.

M.H. Goyns, et al., "Differential Display Analysis of Gene Expression indicates that Age–related Changes are Restricted to a Small Cohort of Genes," *Mercg. Aging Dev.* 101:73–90, 1998.

C.–K. Lee, et al., "Gene Expression Profile of Aging and its Retardation by Caloric Restriction," *Science* 285:1390–1393, 1999.

C.–K. Lee, et al., "Gene–expression Profile of the Adeing Brain in Mice," *Nat. Gene.* 25:294–297, 2000.

Y. Masur, "Systeme Electronique pour Applications," No. 63, 1988–1989.

M. Tresini, et al., "Effects of Donor Age on the Expression of a Marker of Replicative Senescence (EPC–1) in human Dermal Fibroblasts," *J. Cell. Physiol.* 179:11–17, 1999.

R.L. Walford, et al., "Dietary Restriction and Aging: Historical Phases, Mechanisms and Current Directions," *Am. Inst. Nut.* 1650–1654, 1987.

* cited by examiner

*Primary Examiner*—Kenneth R. Horlick
*Assistant Examiner*—Teresa Strzelecka
(74) *Attorney, Agent, or Firm*—Quarles & Brady LLP

(57) ABSTRACT

A method of measuring the biological age of a multicellular organism is disclosed. In one embodiment this method comprises the steps of obtaining a sample of nucleic acid isolated from the organism's organ, tissue or cell and determining the expression pattern of a panel of sequences within the nucleic acid that have been predetermined by either increase or decrease in response to biological aging of the organ, tissue or cell. A method of obtaining biomarkers of aging is also disclosed. This method comprises the step of comparing a gene expression profile of a young multicellular organism subject's organ, tissue or cells; a gene expression profile from a chronologically aged subject's organ, tissue or cell; and a gene expression profile from a chronologically aged but biologically younger subject's organ, tissue or cell and identifying gene expression alterations that are observed when comparing the young subjects and the chronologically aged subjects and are not observed or reduced in magnitude when comparing the young subjects and the chronologically aged but biologically younger subjects.

7 Claims, No Drawings

IDENTIFICATION OF GENETIC MARKERS OF BIOLOGICAL AGE AND METABOLISM

CROSS-REFERENCE TO RELATED APPLICATION

This application claims priority to provisional application No. 60/148,540, filed Aug. 12, 1999, U.S. provisional application No. 60/178,232, filed Jan. 26, 2000 and U.S. provisional application No. 60/211,923 filed Jun. 16, 2000. These provisional applications are incorporated by reference as if fully set forth herein.

STATEMENT REGARDING FEDERALLY SPONSORED RESEARCH AND DEVELOPMENT

This invention was made with United States government support awarded by the following agencies: NIH Grant No: AG11915. The United States has certain rights in this invention.

BACKGROUND OF THE INVENTION

A common feature of most multicellular organisms is the progressive and irreversible physiological decline that characterizes senescence. Although genetic and environmental factors can influence the aging process, the molecular basis of senescence remains unknown. Postulated mechanisms include cumulative damage to DNA leading to genomic instability, epigenetic alterations that lead to altered gene expression patterns, telomere shortening in replicative cells, oxidative damage to critical macromolecules and nonenzymatic glycation of long-lived proteins (S. M. Jazwinski, *Science* 273:54, 1996; G. M. Martin, et al., *Nature Gen.* 13:25, 1996; F. B. Johnson, et al., *Cell* 96:291, 1996; K. B. Beckman and B. N. Ames, *Physiol. Revs.* 78:547, 1998). Factors which contribute to the difficulty of elucidating mechanisms and testing interventions include the complexity of organismal senescence and the lack of molecular markers of biological age (biomarkers). Aging is complex in that underlying mechanisms in tissues with limited regenerative capacities (e.g., skeletal and cardiac muscle, brain), which are composed mainly of postmitotic (non-dividing) cells, may differ markedly from those operative in proliferative tissues. Accordingly, approaches which provide a global assessment of senescence in specific tissues would greatly increase understanding of the aging process and the possibility of pharmaceutical, genetic or nutritional intervention.

Genetic manipulation of the aging process in multicellular organisms has been achieved in Drosophila, through the over-expression of catalase and Cu/Zn superoxide dismutase (W. C. Orr and R. S. Sohal, *Science* 263:1128, 1994; T. L. Parkes, et al., *Nat. Genet.* 19:171, 1998), in the nematode *C. elegans*, through alterations in the insulin receptor signaling pathway (S. Ogg, et al., *Nature* 389:994, 1997; S. Paradis and G. Ruvkun, *Genes Dev.* 12:2488–2498, 1998; H. A. Tissenbaum and G. Ruvkun, *Genetics* 148:703,1998), and through the selection of stress-resistant mutants in either organism (T. E. Johnson, *Science* 249:908, 1990; S. Murakami and T. E. Johnson, *Genetics* 143:1207, 1996; Y. J. Lin, et al., *Science* 282:943, 1998). In mammals, there has been limited success in the identification of genes that control aging rates. Mutations in the Werner Syndrome locus (WRN) accelerate the onset of a subset of aging-related pathology in humans, but the role of the WRN gene product in the modulation of normal aging is unknown (C. E. Yu, et al., *Science* 272:258, 1996; D. B. Lombard and L. Guanrente, *Trends Genet.* 12:283, 1996).

In contrast to the current lack of genetic interventions to retard the aging process in mammals, caloric restriction (CR) appears to slow the intrinsic rate of aging (R. Weindruch and R. L. Walford, *The Retardation of Aging and Disease by Dietary Restriction* (C C. Thomas, Springfield, Ill., 1988; L. Fishbein, Ed., *Biological Effects of Dietary Restriction* (Springer-Verlag, N.Y., 1991; B. P. Yu, Ed., *Modulation of Aging Processes by Dietary Restriction* (CRC Press, Boca Raton, Fla. 1994). Most studies have involved laboratory rodents which, when subjected to a long-term, 25–50% reduction in calorie intake without essential nutrient deficiency, display delayed onset of age-associated pathological and physiological changes and extension of maximum lifespan.

BRIEF SUMMARY OF THE INVENTION

The present invention will allow the evaluation of aging interventions on a molecular and tissue-specific basis through the identification of aging biomarkers. In particular, the use of gene expression profiles allows the measurement of aging rates of target organs, tissues and cells, and to what extent aging is delayed by specific interventions, as determined by quantitative analysis of mRNA abundance. Because aging-related gene expression profiles can be classified in subgroups according to function, the invention also allows for the determination of how function-specific aspects of aging are affected. This particular feature will allow for determination of combination therapies that prevent or reverse most aging related changes in particular organs, tissues, and cells.

In one embodiment, the present invention is a method of measuring the biological age of a multicellular organism comprising the steps of (a) obtaining a sample of nucleic acid isolated from the organism's organ, tissue or cell, wherein the nucleic acid is RNA or a cDNA copy of RNA and (b) determining the expression pattern of a panel of sequences within the nucleic acid that have been predetermined to either increase or decrease in response to biological aging of the organ, tissue or cell. Preferably, the expression patterns of at least ten sequences are determined in step (b) and the organism is a mammal, most preferably a rodent.

In one preferred embodiment of the method described above, the nucleic acid is isolated from a mammalian tissue selected from the group consisting of brain tissue, heart tissue, muscle tissue, skin, liver tissue, blood, skeletal muscle, lymphocytes and mucosa.

In another embodiment the present invention is a method of obtaining biomarkers of aging comprising the steps of: (a) comparing a gene expression profile of a young multicellular organism subject's organ, tissue or cells; a gene expression profile from a chronologically aged (and therefore biologically aged) subject's organ, tissue or cell; and a gene expression profile from a chronologically aged but biologically younger subject's organ, tissue or cell, and (b) identifying gene expression alterations that are observed when comparing the young subjects and the chronologically aged subjects and are not observed or reduced in magnitude when comparing the young subjects and chronologically aged and biologically younger subjects. Preferably, one uses high density oligonucleotide arrays comprising at least 5–10% of the subject's gene expression product to compare the subject's gene expression profile, and caloric restriction to obtain a chronologically aged but biologically younger subject.

In a preferred embodiment of the method described above, the gene expression profile indicates a two-fold or greater increase or decrease in the expression of certain genes in biologically aged subjects. In a more preferred embodiment of the present invention, the gene expression profile indicates a three-fold or greater or, most preferably three-fold or greater, increase or decrease in the expression of certain genes in aged subjects.

In another embodiment, the present invention is a method of measuring biological age of muscle tissue comprising the step of quantifying the mRNA abundance of a panel of biomarkers selected from the group consisting of markers described in the Tables 1, 2, 15 and 16. A method of measuring biological age of brain tissue comprising the step of quantifying the mRNA abundance of a panel of biomarkers selected from the group consisting of markers described in Tables 5, 6, 9, 10, 11, 12, 13 and 14.

In another embodiment, the present invention is a method for screening a compound for the ability to inhibit or retard the aging process in a multicellular organism tissue, organ or cell, preferably mammalian tissue, organ or cell, comprising the steps of: (a) dividing test organisms into first and second samples; (b) administering a test compound to the organisms of the first sample; (c) analyzing tissues, organisms and cells of the first and second samples for the level of expression of a panel of sequences that have been predetermined to either increase or decrease in response to biological aging of the tissue, (d) comparing the analysis of the first and second samples and identifying test compounds that modify the expression of the sequences of step (c) in the first sample such that the expression pattern is indicative of tissue that has an inhibited or retarded biological age.

It is an object of the present invention to evaluate or screen compounds for the ability to inhibit or retard the aging process.

It is also an object of the present invention to measure the biological age of a multicellular organism, such as a mammal in a tissue or cell-specific basis.

It is also an object of the present invention to obtain biomarkers of aging.

Other objects, features and advantage of the present invention will become apparent to one of skill in the art after review of the specification and claims.

DETAILED DESCRIPTION OF THE INVENTION

One of the major impediments to the development of pharmaceutical, genetic or nutritional interventions aimed at retarding the aging process is the lack of a molecular method for measuring the aging process in humans or experimental animals. A suitable biomarker of the aging process should reflect biological age (physiological condition) as opposed to chronological age. Additionally, the biomarker should be amenable to quantitation, and reflect aging-related alterations at the molecular level in the tissue under study. Importantly, any such biomarker must be validated with the use of a model of retarded aging.

Caloric restriction, when started either early in life or in middle-age, represents the only established paradigm of aging retardation in mammals. (R. Weindruch and R. L. Walford, "The Retardation of Aging and Disease by Dietary Restriction" (C. C. Thomas, Springfield, Ill., 1988)) The effects of caloric restriction on age-related parameters are broad: caloric restriction increases mean and maximum lifespan, reduces and delays both spontaneous and induced carcinogenesis, almost completely suppresses autoimmunity associated with aging, and reduces the incidence of several age-induced diseases. (R. Weindruch and R. L. Walford, supra, 1988) Therefore, we expect that the rate of change of most proposed aging biomarkers should be retarded by caloric restriction.

By "biological age" we mean the physiological state of an animal or tissue relative to the physiological changes that occur throughout the animal's lifespan. By "chronological age" we mean the age of an animal as measured by a time scale such as month or years.

Because gene expression patterns are responsive to both intracellular and extracellular events, we reasoned that simultaneous monitoring of thousands of genes on a tissue-specific or organ-specific basis would reveal a set of genes that are altered in expression levels as a consequence of biological aging. Although alterations in gene expression with aging had been previously investigated for some genes, a global analysis of gene expression patterns during aging, and the validation of such patterns as a tool to measure biological age through the use of a model of retarded aging had not been previously performed. Such global analysis is required to identify genes that are expressed differentially as a consequence of aging on different cell types that compose the tissue under study and will allow a quantitative assessment of aging rates.

There exists a large and growing segment of the population in developed countries that is suffering from age-associated disorders, such as sarcopenia (loss of muscle mass), neurodegenerative conditions, and cardiac disease. Therefore, the market for compounds that prevent aging-associated disorders and improve quality of life for the elderly is likely to drive research and development of novel drugs by the pharmaceutical industry. As an example, many drugs, nutraceuticals and vitamins are thought to influence aging favorably, but their use remains limited due to the lack of FDA approval. The inability to assess biological aging in tissues at the molecular level precludes proper animal and human testing of such compounds.

In one embodiment, the invention is a method for measuring the biological aging process of a multicellular organism, such as a mammal, at the organ, tissue or cellular level through the characterization of the organism's gene expression patterns. This method preferably comprises obtaining a cDNA copy of the organism's RNA and determining the expression pattern of a panel of particular sequences (preferably at least 5 sequences, most preferably at least 10 sequences and more preferably at least 20, 30, 40, or 50 sequences) within the cDNA that have been predetermined to either increase or decrease in response to biological aging of the organ, tissue or cell. (We refer to nucleotide sequences with alterartions in expression patterns characteristic of biological age as "biomarkers.") One may characterize the biological age of the organism by determining how many and at what level the biomarkers are altered.

Tables 1–4 and 15–16 describe a specific gene expression profiles determined in skeletal muscle of mice. Tables 1, 2,15 and 16 describe aging-related increases and decreases in gene expression in gastrocnemius of mice. (Tables 1 and 2 were prepared using a high density oligonucleotide array of over 6,300 genes, while Tables 15 and 16 were prepared using a high density oligonucleotide array of 19,000 genes.) Tables 3 and 4 describe caloric restriction related decreases and increases in gene expression. Tables 1 and 2 contain a column ("CR reversal") describing the influence of caloric restriction on the increased or decreased expression. Tables 5–8 describe a similar analysis of the gene expression profile determined neocortex tissue of mice and Tables 9 and 10 describe a gene expression profile determined on the cerebellum tissue in mice. Tables 11–14 describe gene expression profiles determined in mouse heart. (Tables 11 and 12 were prepared with the 19,000 high density oligonucleotide chip, while Tables 13 and 14 were prepared using the less dense gene chip.) From these gene expression profiles, one may select many biomarkers.

For example, in order to either measure or determine biological age in skeletal muscle, one would select markers in Tables 1 and 2 that reflect changes in gene expression that have been shown to be either partially or completely inhibited by caloric restriction in skeletal muscle such as AA0071777, L06444, AA114576, etc. Genes that were not affected by caloric restriction (such as W84988, Table 1) may represent chronological markers or aging, and therefore are less useful for the measurement of aging rates. One may determine which genes are or are not affected by caloric restriction by examination of the "CR reversal" lane of Tables 1 or 2.

If one wished to examine a tissue, organ or cell that is not represented in Tables 1–16, one would prepare samples and tabulate results from those samples as described below in the Examples. In this manner, one may examine any tissue, organ or cell for biological aging. Preferably, one would wish to examine a tissue selected from the group consisting of brain tissue, heart tissue, muscle tissue, skin, liver tissue, blood, lymphocytes, skeletal tissue and mucosa.

For example, choosing markers from Tables 1 and 2 to examine the efficacy of a test compound in aging prevention, one could design a PCR-based amplification strategy or a DNA microarray hybridization strategy to quantify the mRNA abundance for markers W08057, AA114576, 11071777, 11106112, D29016 and M16465 as a function of aging, using animals of several age groups, such as 6 months, 12 months, 18 months, 24 months and 30 months. (The marker designations refer to Gene Bank accession number entries.) A second set of animals would be given a test compound intended to slow the aging process at 10 months of age (middle age). Animals from the experimental group would be sacrificed or biopsied at the ages of 12 months, 18 months, 24 months and 30 months. If the test compound is successful, the normal aging-related alterations in expression of these particular markers will be prevented or attenuated.

One would follow the same protocol in using the other tables for marker selection. One would match the tissue to be analyzed with the appropriate table. For example, if one were analyzing muscle tissue, one might choose markers from Tables 1 and 2.

In another embodiment, the present invention is a method of obtaining and validating novel mammalian biomarkers of aging. Preferably, this method comprises the steps of comparing the gene expression profile from a young subject's organ, tissue or cells with samples from individuals that are both chronologically and biologically aged. This is followed by comparison of the gene expression profile of the chronologically and biologically aged individuals with that of individuals that display similar chronological ages, but a younger biological age, such as animals under caloric restriction. Gene expression alterations that are prevented or retarded by caloric restriction represent markers of biological age, as opposed to chronological age.

In one version of this embodiment, one would preferably use high density oligonucleotide arrays representing at least 5–10% of the subject's genes, as described in Lee, et al. at Science 285(5432):1390–1393, 1999 and Lee, et al., Nat. Genet. 25(3):294–297, 2000. (Both Lee, et al., supra, 1999 and Lee, et al., supra, 2000 are incorporated by reference as if fully set forth herein.)

For example, Lee, et al., supra, 1999 details the comparison between gastrocnemius muscle from 5 month (young) and 30 month (aged) mice, and 30 month mice under caloric restriction. Lee, et al., supra, 1999 disclose that of the 6500 genes surveyed in the oligonucleotide array, 58 (0.9%) displayed a greater than 2-fold increase in expression levels as a function of age and 55 (0.8%) displayed a greater than 2-fold decrease in expression. The most substantial expression change was for the mitochondrial sarcomeric creatine kinase (Mi-CK) gene (3.8-fold). Sequences that display a greater than three-fold alteration (increase or decrease) with aging, which are prevented or restricted by caloric restriction, such as W08057, AA114576, AA071777, AA106112, D29016, M16465, are likely to be particularly good aging biomarkers.

Lee, et al., supra, 2000 describes the comparison between cDNAs isolated from neocortex tissue for the same three groups of mice described above. Lee, et al., supra, 2000 disclose that of the 6347 genes surveyed, 63 (1%) displayed a greater than 1.7-fold increase in expression levels with aging in the neocortex, whereas 63 genes (1%) displayed a greater than 2.1-fold increase in expression in the cerebellum. Functional classes were assigned and regulatory mechanisms inferred for specific sets of alterations (see Tables 5–10). Of these, 20% (13/63), and 33% (17–51) could be assigned to an inflammatory response in the neocortex and cerebullum, respectively. Transcriptional alterations of several genes in this category were shared by the two brain regions, although fold-changes tended to be higher in the cerebellum, perhaps due to reduced tissue size and/or reduced heterogeneity at the cellular level. These transcriptional alterations include the microglial and macrophage migration factor Mps1 and the Cd40L receptor, which is a mediator of the microglial activation pathway. Also induced was Lysozyme C and beta(2) microglobulin which are markers of inflammation in the human CNS. Interestingly, a concerted induction of the complement cascade components C4, C1qA, C1qB and C1qC was observed, a part of the humoral immune system involved in inflammation and cytolysis.

In another embodiment, the present invention is a method of screening a test compound for the ability to inhibit or retard the aging process in mammalian tissue. In a typical example of this embodiment, one would first treat a test mammal with a test compound and then analyze a representative tissue of the mammal for the level of expression of a panel of biomarkers. Preferably, the tissue is selected from the group consisting of brain tissue, heart tissue, muscle tissue, blood, skeletal muscle, mucosa, skin and liver tissue. One then compares the analysis of the tissue with a control, untreated mammal and identifies test compounds that are capable of modifying the expression of the biomarker sequences in the mammalian samples such that the expression is indicative of tissue that has an inhibited or retarded biological age. This expression pattern would be more similar to an expression pattern found in biologically younger subjects.

As an example, a group of young rodents (mice) would be divided into a control and a test group. The test group would receive a test compound as a dietary supplement added to food from age 5 months to 30 months, whereas the control group would receive a standard diet during this time period. At age 30 months, several tissues would be collected from animals from each group, and a gene expression profile would be obtained. Each animal's gene expression profile would be compared to that of a 5 month (young) animals receiving the standard diet. One would then examine if, for any of the organs investigated, the gene expression pattern of the animals receiving the test compound was more similar to that of young animals, compared to the experimental group that received a standard diet.

In another embodiment, the present invention is a method of detecting whether a test compound mimics the gene profile induced by caloric restriction. This method typically comprises the steps of exposing the mammal to a test compound and measuring the level of a panel of biomarkers. One then determines whether the expression pattern of the tissue mimics the expression pattern induced by caloric restriction.

For example, if one wished to examine skeletal muscle, the test compound would be analyzed for induction of genes observed to be induced by caloric restriction in Tables 3 and 4.

EXAMPLES

1. In General

In order to test our hypothesis, we performed gene expression profiling of over 6300 genes in skeletal muscle, neocortex tissue, and cerebellum tissue and 19,000 genes in skeletal muscle and heart tissue of 5-month and 30-month old C57BI6 mice, using high density oligonucleotide arrays. We found that a number of genes demonstrated alterations in gene expression profile as a function of chronological age and that these genes were broadly divided into a few classes listed in the Tables, such as stress response, energy metabolism, biosynthesis, protein metabolism and neuronal growth.

In order to validate the use of gene expression profiles as biomarkers of biological age, we investigated the role of caloric restriction, the only intervention known to retard the aging process in mammals, on gene expression profiles. Our analysis demonstrated that 30-month old calorically restricted animals display either complete or partial prevention of most aging associated alterations in gene expression, validating the use of gene expression profiles as a biomarkers of the aging process. In the process we have discovered a gene expression profile that is specifically associated with caloric restriction. We believe that this profile provides genetic markers for this metabolic state.

In like fashion, the present invention allows the determination of biological age in any organism through the determination of age-related variations in mRNA abundance. Such determination can be achieved through generation of cDNA from the mRNA of the organism and quantification of the cDNA product through hybridization to DNA microarrays, preferably as described here. Alternatively, any technique that allows for the quantitative determination of mRNA abundance may be used, such as quantitative PCR, Northern blotting and RNAse protection assays. 2. Experimental Protocols Details on the methods employed to house and feed male C57BL/6 mice, a commonly used model in aging research with an average lifespan of ~30 months, were recently described (T. D. Pugh, et al., Cancer Res. 59:642, 1999). Briefly, mice were purchased from Charles River Laboratories (Wilmington, Mass.) at 1.5 months of age. After receipt in Madison, the mice were housed singly in the specific pathogen-free Shared Aging Rodent Facility at the Madison Veterans Administration Geriatric Research, Education and Clinical Center, and provided a non-purified diet (PLI5001 (Purina Labs, St. Louis, Mo.) and acidified water ad libitum for one week. The mice were then allocated into two groups and fed one of two nearly isocaloric (~4.1 kcal/g), semi-purified diets. Each mouse in the control group was fed 84 kcal/week of the control diet (TD91349 (Teklad, Madison, Wis.)) which is ~5–20% less than the range of individual ad libitum intakes. This dietary intake was used so that the control mice were not obese and retained motor activity up to the age of sacrifice. Each mouse subjected to CR was fed 62 kcal/week of the restricted diet (TD9351 (Teklad, Madison, Wis.)), resulting in a 26% reduction of caloric intake. The latter diet was enriched in protein, vitamins and minerals such that caloric restriction (CR) and control mice were fed nearly identical amounts of these components. The fat component, corn oil, was at the same level (13.5%) in both diets, leading to a 26% reduction in fat intake for the calorie-restricted mice. The adult body weights of the mice averaged ~32 g for controls and ~23 g for those on CR. Mice were euthanized by rapid cervical dislocation, autopsied to exclude animals showing overt disease, and the gastrocnemius muscle was removed from each limb, combined in a micocentrifuge tube, and immediately flash-frozen in liquid nitrogen and then stored at ~80° C. All aspects of animal care were approved by the appropriate committees and conformed with institutional guidelines.

Total RNA was extracted from frozen tissue using TRIZOL reagent (Life Technologies) and a power homogenizer (Fisher Scientific) with the addition of chloroform for the phase separation before isopropyl alcohol precipitation of total RNA. Poly(A)$^+$ RNA was purified from the total RNA with oligo-dT linked Oligotex resin (Qiagen). One microgram of poly(A)$^+$ RNA was converted into double-stranded cDNA (ds-cDNA) using SuperScript Choice System (Life Technologies) with an oligo dT primer containing a T7 RNA polymerase promoter region (Genset). After second strand synthesis, the reaction mixture was extracted with phenol/chloroform/isoamyl alcohol. Phase Lock Gel (5 Prime→3 Prime, Inc.) was used to increase ds-cDNA recovery. The ds-cDNA was collected by ethanol precipitation. The pellet was resuspended in 3 $\mu$l of DEPC-treated water. In vitro transcription was performed using a T7 Megascript Kit (Ambion) with 1.5 $\mu$l of ds-cDNA template in the presence of a mixture of unlabeled ATP, CTP, GTP, and UTP and biotin-labeled CTP and UTP (bio-11-CTP and bio-16-UTP (Enzo)). Biotin-labeled cRNA was purified using a RNeasy affinity column (Quiagen). The amount of biotin-labeled cRNA was determined by measuring absorbance at 260 nm. Biotin-labeled cRNA was fragmented randomly to sizes ranging from 35 to 200 bases by incubating at 94° C. for 35 minutes in 40 mM Tris-acetate pH 8.1, 100 mM potassium acetate, and 30 mM magnesium acetate. The hybridization solutions contained 100 mM MES, 1 M (Na$^{3o}$), 20 mM EDTA, and 0.1% Tween 20. In addition, the hybridization solutions contained 50 pM oligonucleotide B2 (a biotin-labeled control oligonucleotide used for making grid alignments), 0.1 mg/mL herring sperm DNA, and 0.5 mg/mL acetylated BSA. The final concentration of fragmented cRNA was 0.05 $\mu$g/$\mu$l in the hybridization solutions. Hybridization solutions were heated to 99° C. for 5 minutes followed by 45° C. for 5 minutes before being placed in the gene chip. 10 $\mu$g of cRNA was placed in the gene chip. Hybridizations were carried out at 45° C. for 16 hours with mixing on a rotisserie at 60 rpm. Following hybridization, the hybridization solutions were removed, and the gene chips were installed in fluidics systems for wash and stain. The fluidics system (Affymetrix GeneChip Fluidics tation 400) performed two post-hybridization washes (a non-stringent wash and a stringent wash), staining with streptavidin-phycoerythrin, and one post-stain wash. The gene chips were read at a resolution of 6 μm using a Hewlett Packard Gene array scanner. Data collected from two scanned images were used for the analysis.

Detailed protocols for data analysis of Affymetrix microarrays and extensive documentation of the sensitivity and quantitative aspects of the method have been described (D. J. Lockhart, *Nature Biotech.* 14:1675, 1996). The Affymetrix GeneChip MU6500 set was derived from selected genes and ESTs from the Aug. 15, 1996 release of GeneBank. Briefly, each gene is represented by the use of ~20 perfectly matched (PM) and mismatched (MM) control probes. The MM probes act as specificity controls that allow the direct subtraction of both background and cross-hybridization signals. The number of instances in which the PM hybridization signal is larger than the MM signal is computed along with the average of the logarithm of the PM:MM ratio (after background subtraction) for each probe set. These values are used to make a matrix-based decision concerning the presence or absence of an RNA molecule. All calculations are performed by Affymetrix software. To determine the quantitative RNA abundance, the average of the differences representing PM minus MM for each gene-specific probe family is calculated, after discarding the maximum, the minimum, and any outliers beyond three standard deviations. For example, to calculate fold changes (FC) between data sets obtained from young (y) vs. old (o) mice, the following formula was used:

$$FC = \frac{SI_o - SI_y}{\text{the smallest of either } SI_y \text{ or } SI_o} + 1 \text{ if } SI_o \geq SI_o \text{ or } -1 \text{ if } SI_o < SI_y$$

Where $SI_o$ is the average signal intensity from a gene-specific probe family from an old mouse and $SI_y$ is that from a young mouse.

Alternatively, $Q_{factor}$, a measure of the non-specific fluorescence intensity background, is larger the smallest of either $SI_y$ or $SI_o$, the FC is calculated as:

$$FC = \frac{SI_o - SI_y}{Q_{factor}}$$

The $Q_{factor}$ is automatically calculated for different regions of the microarray, and therefore minimizes the calculation of spurious fold changes. Average of pair-wise comparisons were made between study groups, each composed of three animals using Excel software. As an example, each 5-month-old mouse was compared to each 30-month-old mouse generating a total of nine pair-wise comparisons.

The murine 19K gene chip allows one to monitor more than 19,000 clustered murine EST transcripts selected from the TIGR (The Institute for Genome Research) database. This database is created by assembling ESTs into virtual transcripts called tentative mouse consensus sequences (Tcs). These sequence contigs are assigned a TC (tentative mouse consensus) number. Therefore, each TC number represents a unique transcript and allows one to check or obtain the sequence from the TIGR mouse gene index.

3. Results

The results of our analysis are shown below in Tables 1–16. Tables 1–4 and 15–16 are the result of the analysis of mouse gastrocnemias muscle. Tables 1 and 15 describe aging-related increases in gene expression, Tables 2 and 16 describe aging-related decrease in gene expression, Table 3 describes caloric restriction related increases, and Table 4 describes caloric restriction related decreases in gene expression. Tables 5–10 describe results obtained using mouse brain tissue. Table 5 describes aging-related increases in gene expression in neocortex, Table 6 describes aging-related decreases in gene expression in neocortex, Table 7 describes caloric restriction related increases in gene expression in neocortex, Table 8 describes caloric restriction related decreases in gene expression in neocortex, Table 9 describes aging-related increases in gene expression in the cerebellum, and Table 10 describes aging-related decreases in gene expression in the cerebellum.

Tables 11–14 are the result of the analysis of mouse heart muscle. Tables 11 and 12, obtained by use of the Mu19K Gene Chip, disclose up-regulated and down-regulated aging-related genes. Tables 13 and 14, obtained from the Mu6500 Gene Chip, disclose up-regulated and down-regulated aging-related genes.

TABLE 1

Aging-related increases in gene expression in gastrocnemius muscle of C57BL/6 mice*

| ORF | Δ Age (fold) | Gene | Class/Function | CR Reversal |
|---|---|---|---|---|
| AA106112 | 3.8 | Mitochondrial Sarcomeric Creatine Kinase | Energy Metabolism/ATP generation | C |
| AA071777 | 3.8 | Synaptic Vesicle Protein 2 | Growth Factor/Neurite extension | 51% |
| Y00004 | 3.6 | Ypt 1/ras-related GTP Binding Protein | Transport/Protein trafficking | C |
| W10855 | 3.5 | Methyl CpG Binding Protein | DNA metabolism/gene silencing | C |
| W08057 | 3.5 | Heat Shock 27 kDa Protein | Stress Response/Chaperone | C |
| M17790 | 3.5 | Serum Amyloid A Isoform 4 | Stress Response/Unknown | N |
| L06444 | 3.5 | GDF-9 | Growth Factor/Unknown | 50% |
| AA114576 | 3.4 | Heat Shock 71 kDa Protein | Stress Response/Chaperone | C |
| W84988 | 3.3 | Transcription Regulatory Protein SWI3 | Transcriptional Factor/Unknown | N |
| X64587 | 3.2 | U2AF | RNA Metabolism/Splicing Factor | C |
| D87902 | 3.2 | ARF5 | Transport/ADP-ribosylation | 87% |
| U19118 | 3.0 | LRG-21 | Transcriptional Factor/Macrophage activation | 42% |
| AA068057 | 2.9 | RabB | Signal Transduction/Unknown | C |
| U05837 | 2.9 | Beta-Hexosaminidase | Catabolism/Lysosomal enzyme | C |
| W85446 | 2.8 | Protein Kinase C Inhibitor 1 Homolog | Signal Transduction/Unknown | 74% |

TABLE 1-continued

Aging-related increases in gene expression in gastrocnemius muscle of C57BL/6 mice*

| ORF | Δ Age (fold) | Gene | Class/Function | CR Reversal |
|---|---|---|---|---|
| AA060167 | 2.8 | Pre-B Cell Enhancing Factor Precursor | Growth Factor/Cytokine | C |
| M37760 | 2.7 | Serine-2 Ultrahigh Sulfur Protein | Unknown | 45% |
| AA096992 | 2.7 | G25K GTP-Binding Protein | Signal Transduction/Unknown | N |
| AA008255 | 2.7 | Adaptin Complex Small Chain Homolog | Unknown | 37% |
| AA166502 | 2.6 | EIF-4A-II | RNA Metabolism/RNA helicase | N |
| X66602 | 2.6 | POU-domain protein | Transcriptional Factor/Unknown | N |
| X79828 | 2.6 | NK 10 | Transcriptional Factor/Unknown | N |
| V00719 | 2.6 | Alpha-Amylase-1 | Energy Metabolism/Starch metabolism | N |
| L28177 | 2.6 | GADD45 | Stress Response/Cell cycle checkpoint | 77% |
| W50941 | 2.5 | Nucleotide Pyrophosphatase | Unknown | N |
| X53257 | 2.5 | Neurotrophin-3 | Growth Factor/Reinnervation of muscle | 50% |
| M74570 | 2.4 | Aldehyde Dehydrogenase II | Stress Response/Aldehyde detoxification | 29% |
| D49473 | 2.4 | Sox17 | Transcriptional Factor/Unknown | 86% |
| AA117284 | 2.3 | Zinc Finger Protein 43 (HTF6) | Transcriptional Factor/Unknown | N |
| W63835 | 2.3 | Beta-centractin | Structural/contractility | 60% |
| AA089097 | 2.2 | Phosphatidylcholine-transfer Protein | Transport/Lipid turnover | C |
| AA059662 | 2.2 | Protease Do Precursor | Stress Response/Protease | C |
| L22482 | 2.2 | HIC-5 | Stress Response/Senescence and differentiation | C |
| X78197 | 2.2 | AP-2 Beta | Transcriptional Factor/Neurogenesis | N |
| AA059664 | 2.2 | IGF Binding Protein | Growth Factor/Cellular senescence | C |
| V00714 | 2.2 | Alpha Globin | Structural/Hemoglobin component | C |
| X99963 | 2.2 | rhoB | Stress Response/Unknown | 87% |
| AA014024 | 2.1 | Dynactin | Transport/Neuronal transport | 55% |
| X65627 | 2.1 | TNZ2 | Stress Response/RNA metabolism | 64% |
| X95503 | 2.1 | GTP-Binding Protein (IRG-47) | Signal Transduction/Unknown | 85% |
| V00727 | 2.1 | FBJ-MuSV | Provirus/None | C |
| X12807 | 2.1 | pp2.5 | Unknown | C |
| W08049 | 2.1 | MAGP | Structural/Microfibril glycoprotein | N |
| AA066425 | 2.1 | CO-029 | Structural/Cell surface glycoprotein | N |
| W82998 | 2.1 | POLYA + RNA Export Protein | RNA Metabolism/RNA export | 44% |
| X89749 | 2.1 | mTGIF | Transcriptional Factor/Neuronal differentiation | C |
| L07918 | 2.1 | GDP-Dissociation Inhibitor | Transport/membrane dynamics | N |
| X63190 | 2.1 | PEA3 | Transcriptional Factor/Response to muscle injury | C |

*The influence of CR on the increased expression with age of specific ORFs is denoted as either C (complete, ≥90%), N (none) or partial (≥20%, percentage effect indicated).

TABLE 2

Aging-related decreases in gene expression in gastrocnemius muscle of C57BL/6 mice*

| ORF | Δ Age (fold) | Gene | Class/Function | CR Reversal |
|---|---|---|---|---|
| D29016 | −6.4 | Squalene Synthase | Biosynthesis/Cholesterol/fatty acid synthesis | 52% |
| AA106126 | −4.9 | Myosin Heavy Chain, Perinatal | Structural Protein/Muscle contraction | C |
| D31898 | −4.4 | Protein Tyrosine Phosphatase, PTPBR7 | Signal Transduction/Unknown | 79% |
| U29762 | −4.3 | Albumin Gene D-Box Binding Protein | Transcriptional Factor/Albumin synthesis | 85% |
| AA061310 | −4.1 | Mitochondrial LON Protease | Energy Metabolism/Mitochondrial biogenesis | C |
| AA162443 | −3.6 | Protein Phosphatase PP2a | Signal Transduction/Unknown | C |
| M89797 | −3.5 | Wnt-4 | Signal Transduction/Unknown | 72% |
| M16465 | −3.4 | Calpactin I Light Chain | Signal Transduction/Calcium effector | C |
| X74134 | −3.2 | Ovalbumin Transcription Factor I | Transcriptional Factor/Unknown | N |
| U08020 | −3.2 | Alpha 1 Type 1 Collagen | Structural Protein/Extracellular matrix | N |
| X58251 | −3.1 | Pro-alpha-2(I) Collagen | Structural Protein/Extracellular matrix | N |
| AA138226 | −3.1 | Clathrin Light Chain B | Intracellular Transport/Vesicle transport | C |
| X85214 | −3.0 | Ox40 | Signal Transduction/T Cell activation | 50% |
| D76440 | −2.9 | Necdin | Growth Factor/neuronal growth suppressor | 47% |
| AA107752 | −2.9 | EF-1-Gamma | Protein Metabolism/Protein synthesis | 63% |
| W55037 | −2.9 | Alpha Enolase | Energy Metabolism/Glycolysis | 68% |
| X74134 | −2.8 | COUP-TFI | Transcription Factor/Unknown | 28% |
| U06146 | −2.8 | Desintegrin-related Protein | Unknown | 28% |
| U39545 | −2.8 | BMP8b | Growth Factor/Unknown | C |
| X75014 | −2,7 | Phox2 Homeodomain Protein | Transcriptional Factor/Neuronal differentiation and survival | 65% |

TABLE 2-continued

Aging-related decreases in gene expression in gastrocnemius muscle of C57BL/6 mice*

| ORF | Δ Age (fold) | Gene | Class/Function | CR Reversal |
|---|---|---|---|---|
| U22031 | −2.6 | 20S Proteasome Subunit | Protein Metabolism/Protein turnover | 44% |
| U70210 | −2.5 | TR2L | Transcriptional Factor/Apoptosis modulator | N |
| X76652 | −2.5 | 3f8 | Structural Protein/Neuronal adhesion | N |
| W54288 | −2.5 | PKCSH | Signal Transduction/Unknown | C |
| M81475 | −2.5 | Phosphoprotein Phosphatase | Energy Metabolism/Glycogen metabolism | C |
| U22394 | −2.3 | mSin3 | Transcriptional Factor/Inhibitor of cell proliferation | 46% |
| M83336 | −2.3 | gp130 | Signal Transduction/Unknown | 77% |
| L34611 | −2.3 | PTHR | Signal Transduction/Ca homeostasis | N |
| X52046 | −2.3 | Pro-Alpha1 (III) Collagen | Structural Protein/Extracellular matrix | N |
| L2450 | −2.2 | DNA Binding-protein | Unknown | 58% |
| AA103356 | −2.2 | Calmodulin | Signal Transduction/Calcium effector | N |
| L37092 | −2.2 | p130PITSL Cyclin-kinase | DNA Metabolism/Cell cycle control | N |
| AA061604 | −2.2 | Ubiquitin Thiolesterase | Protein Metabolism/Protein turnover | C |
| AA139680 | −2.2 | DNA Polymerase Alpha Primase | DNA Metabolism/DNA replication | N |
| AA034842 | −2.1 | ERV1 | DNA Metabolism/Maintenance of MtDNA | 46% |
| M21285 | −2.1 | Stearoyl-CoA Desaturase | Biosynthesis/PUFA synthesis | C |
| U11274 | −2.1 | PmuAUF1-3 | RNA Metabolism/RNA degradation | N |
| U73744 | −2.1 | HSP70 | Stress Response/Chaperone | N |
| J03398 | −2.1 | MDR | Membrane Protein/Unknown | N |
| AA145829 | −2.1 | 26S Proteasome Component TBP1 | Protein Metabolism/Protein turnover | C |
| M32240 | −2.1 | GAS3 | Growth Factor/Apoptosis and growth arrest | 55% |
| L00681 | −2.1 | Unp Ubiquitin Specific Protease | Protein Metabolism/Protein turnover | N |
| U34277 | −2.0 | PAF Acetylhydrolase | Unknown | N |
| U35741 | −2.0 | Rhodanese | Protein Metabolism/Mitochondrial protein folding | C |
| W53731 | −2.0 | Signal Recognition Particle Receptor | Intracellular Transport/Protein trafficking | C |
| AA044497 | −2.0 | Zinc Finger Protein 32 | Transcriptional Factor/Unknown | 40% |
| L27842 | −2.0 | PMP35 | Energy Metabolism/Peroxisome assembly | 60% |
| AA106406 | −2.0 | ATP Synthase A Chain | Energy Metabolism/ATP synthesis | N |
| AA041826 | −2.0 | IPP-2 | Energy Metabolism/Glycogen Metabolism | C |

*The influence of CR on the increased expression with age of specific ORFs is denoted as either C (complete, ≧90%), N (none) or partial (≧20%, percentage effect indicated).

TABLE 3

Caloric restriction-related increases in gene expression

| ORF | Δ CR (fold) | Gene | Class/Function |
|---|---|---|---|
| U68267 | 9.6 | Myosin Binding Protein H (MyBP-H) | Structural/Myofibril interactions |
| X13135 | 4.7 | Fatty Acid Synthase | Biosynthesis/Fatty acid synthesis |
| U05809 | 4.5 | LAF1 Transketolase | Energy Metabolism/Carbohydrate metabolism |
| W53351 | 4.1 | Fructose-bisphosphate Aldolase | Energy Metabolism/Glycolysis |
| M15501 | 3.5 | Cardiac Muscle Alpha Actin | Structural/Muscle contraction |
| AA071776 | 3.5 | Glucose-6-Phosphate Isomerase | Energy Metabolism/Glycolysis |
| AA073283 | 3.3 | Cardiac Muscle Myosin Beta-Actin | Structural/Contractile protein |
| AA138226 | 2.9 | Clathrin Light Chain B | Transport/Axonal transport |
| L42115 | 2.9 | Insulin-Activated Amino Acid Transporter | Transport/Aminoacid transport |
| U37222 | 2.8 | Adipocyte Complement-Related Protein (Acrp30) | Growth Factor/Unknown |
| W89939 | 2.7 | FK506-Binding Protein (FKBP-12) | Signal Transduction/Neuronal regeneration |
| X16314 | 2.5 | Glutamine Synthetase | Biosynthesis/Glutamine synthesis |
| AA080277 | 2.5 | Sodium Potassium ATPase Alpha-2 Chain | Membrane Protein/Ion pump |
| W30250 | 2.5 | Myosin Light Chain 1 | Structural/Contractile protein |
| AA137659 | 2.4 | Cytochrome P450-IIC12 | Biosynthesis/Steroid biosynthesis |
| AA031112 | 2.4 | ZFP-37 | Transcriptional Factor/Unknown |
| U34295 | 2.3 | Glucose Dependent Insulinotropic Polypeptide | Energy Metabolism/Insulin sensitizer |
| W54288 | 2.3 | Protein Kinase-C Substrate (80K-H) | Signal Transduction/AGE receptor |

TABLE 3-continued

Caloric restriction-related increases in gene expression

| ORF | Δ CR (fold) | Gene | Class/Function |
|---|---|---|---|
| U01841 | 2.3 | Peroxisome Proliferator Receptor Gamma (PPAR) | Energy Metabolism/Insulin sensitizer |
| AA109527 | 2.3 | Actin 1 | Structural/Contractile protein |
| AA145829 | 2.3 | 26S Protease Subunit TBP-1 | Protein Metabolism/26S proteasome component |
| Y00137 | 2.3 | Lymphotoxin-Beta | Signal Transduction/Cytokine |
| AA107752 | 2.2 | Elongation Factor 1-gamma | Protein Metabolism/Protein synthesis |
| AA016431 | 2.2 | Keratinocyte Lipid-binding Protein | Unknown/Fatty acid binding |
| M93275 | 2.1 | Adipose Differentiation Related Protein (ADFP) | Unknown |
| W53731 | 2.1 | Signal Recognition Particle Receptor Alpha Subunit | Protein Metabolism/Protein synthesis |
| U60328 | 2.1 | Proteasome Activator PA28 Alpha Subunit | Protein Metabolism/Protein turnover |
| W78478 | 2.1 | Gamma E-crystallin | Unknown |
| X67083 | 2.1 | Chop-10 (gadd153) | Stress-Response/Growth arrest |
| U40189 | 2.1 | Neuropeptide Y | Unknown |
| AA020281 | 2.1 | Progesterone Reductase | Metabolic/Progesterone metabolism |
| AA022083 | 2.0 | Huntingtin | Unknown |
| X59990 | 2.0 | mCyP-S1 (Cyclophilin) | Protein Metabolism/Protein folding |
| X56548 | 2.0 | Purine Nucleoside Phosphorylase | Biosynthesis/Purine turnover |
| L28116 | 2.0 | PPAR Delta | Energy Metabolism/Peroxisome induction |
| U43319 | 2.0 | Frizzled 6 | Unknown |
| X14432 | 2.0 | Thrombomodulin | Unknown |
| L32973 | 2.0 | Thymidylate Kinase | Biosynthesis/dTTP sythesis |
| D76440 | 1.9 | Necdin | Growth Factor/Neuronal growth suppressor |
| L36860 | 1.9 | GCAP | Signal Transduction/Calcium-binding regulatory protein |
| W08293 | 1.9 | Translocon-Associated Protein Delta | Protein Metabolism/Protein translocation |
| AA041826 | 1.9 | Protein Phosphatase Inhibitor 2 (IPP-2) | Energy Metabolism/Inhibition of glycogen synthesis |
| D42083 | 1.9 | Fructose 1,6-bisphosphatase | Energy Metabolism/Gluconeogenesis |
| AA008737 | 1.9 | Peroxisomal Protein PAS8 | Transport/Peroxisome targeting |
| W57495 | 1.8 | 60S Ribosomal Protein L23 | Protein Metabolism/Protein synthesis |
| D83585 | 1.8 | Proteasome Z Subunit | Protein Metabolism/Protein turnover |
| M13366 | 1.8 | Glycerophosphate Dehydrogenase | Energy Metabolism/Electron transport to mitochondria |
| U37091 | 1.8 | Carbonic Anhydrase IV | Energy Metabolism/$CO_2$ disposal |

*The genes listed on this table were not influenced by age. Reversal of aging-associated changes are listed in Tables 1 and 2. Energy Metabolism and Biosynthetic classes are highlighted in blue.

TABLE 4

Caloric restriction-related decreases in gene expression

| ORF | Δ DR (fold) | Gene | Class/Function |
|---|---|---|---|
| AA062328 | -3.4 | DnaJ Homolog 2 | Stress Response/Chaperone |
| X03690 | -2.5 | Ig Heavy Chain Constant Region mu(b) | Immune Function/Antibody |
| U60453 | -2.3 | Ezh1 (Zeste Homolog 2) | Transcriptional Factor/Gene silencing |
| M83380 | -2.3 | relB | Transcriptional Factor/Unknown |
| D38613 | -2.1 | 921-L Presynaptic Protein | Unknown |
| X82457 | -2.0 | es64 | Unknown |
| U35646 | -2.0 | Aminopeptidase | Protein Metabolism/Protein turnover |
| W13412 | -1.9 | ATP Synthase Coupling Factor B | Energy Metabolism/ATP synthesis |
| M92416 | -1.9 | FGF-6 | Growth Factor/Muscle regeneration |
| U58497 | -1.9 | mp86 (Mnb Protein Kinase) | Signal Transduction/Unknown |
| L29454 | -1.9 | Fbn-1 (Fibrillin) | Stuctural/Microfibril organization |
| U56773 | -1.9 | Pelle-like Protein Kinase | Signal Transduction/Unknown |
| D49439 | -1.9 | TFIID Subunit p80 | Transcriptional Factor/Unknown |
| D31943 | -1.9 | Inducible SH2-Containing Protein | Growth Factor/Cytokine |
| U47737 | -1.9 | TSA-1 | Signal Transduction/T cell function |

TABLE 4-continued

Caloric restriction-related decreases in gene expression

| ORF | Δ DR (fold) | Gene | Class/Function |
|---|---|---|---|
| X63023 | −1.9 | Cytochrome P-450-IIIA | Stress Response/Detoxification |
| X53476 | −1.8 | HMG-14 | DNA Metabolism/Chromatin remodeling |
| L33768 | −1.8 | JAK3 | Signal Transduction/T cell function |
| U03283 | −1.8 | Cyp1b1 Cytochrome P450 | Stress Response/Detoxification |
| U14390 | −1.8 | Aldehyde Dehydrogenase-3 | Stress Response/Detoxification |
| U75530 | −1.8 | FHAS-II | Protein Metabolism/Translation inhibitor |
| X13605 | −1.8 | Histone H3.3 | DNA metabolism/Chromatin remodeling |
| U65313 | −1.8 | G3BP | DNA metabolism/Helicase |
| AA062349 | −1.8 | P31 | Protein Metabolism/Protein turnover |
| X76850 | −1.8 | MAPKAP2 | Stress Response/Unknown |
| D43694 | −1.8 | Math-1 | Transcription Factor/Neuronal differentiation |
| U66887 | −1.8 | RAD50 | DNA Metabolism/DNA repair |
| M83219 | −1.8 | MRP14 | Growth Factor/Inflammation |
| Z14986 | −1.8 | SAMDC | Biosynthesis/Polyamine synthesis |
| W17516 | −1.8 | NEDD8 | Unknown |
| D78641 | −1.7 | Membrane Glycoprotein | Unknown |
| D26123 | −1.7 | Carbonyl Reductase | Unknown |
| U71205 | −1.7 | rit | Signal Transduction/Unknown |
| U31510 | −1.7 | ADP-ribosyltransferase | Protein Metabolism/ADP-ribosylation |
| L4406 | −1.7 | Hsp105-beta | Stress Response/Chaperone |
| AA059718 | −1.7 | DNA Polymerase Beta | DNA Metabolism/DNA repair |
| D16464 | −1.7 | HES-1 | Transcription Factor/Neuronal differentiation |
| D87963 | −1.7 | ETFR-1 | Transcriptional Factor/Unknown |
| U12236 | −1.7 | Alpha M290 Integrin | Signal Transduction/Cell and matrix adhesion |
| X98848 | −1.7 | 6-phosphofructo-2-kinase | Energy Metabolism/glycolysis |
| W41974 | −1.7 | ATP-Dependent RNA Helicase-Homolog | RNA Metabolism/Unknown |
| X75285 | −1.6 | Fibulin-2 | Structural/Basement membrane |
| M96265 | −1.6 | GALT | Energy Metabolism/Glycolysis |
| D67015 | −1.6 | 97kDa Nuclear Pore Targeting Complex | Transport/Nuclear import |
| AA002750 | −1.6 | 5-lypoxygenase Activating Protein (FLAP) | Biosynthesis/Leukotriene synthesis |
| X93357 | −1.6 | SYT | Transcriptional Factor/Unknown |
| W13191 | −1.6 | Thyroid Hormone Receptor Alpha-2 | Metabolic/Thyroid hormone receptor |
| U43206 | −1.6 | Phosphatidylethanolamine Binding Protein | Signal Transduction/Unknown |
| W11169 | −1.6 | SUI1ISO1 | Protein Metabolism/Translation initiation factor |
| W42234 | −1.6 | XPE | DNA Metabolism/DNA repair |
| W08897 | −1.6 | Seryl-tRNA Synthetase | Protein Metabolism/Protein synthesis |
| AA027739 | −1.6 | Heterogeneous Nuclear Ribonucleoprotein K | Transcriptional Factor/Unknown |

*The genes listed on this table were not influenced by age. Reversal of aging-associated changes are listed in Tables 1 and 2. DNA Repair and Stress Response classes are highlighted in green.

TABLE 5

Aging-related increases in gene expression in neocortex of C57BL/6 mice*

| ORF | Δ Age (fold) | SE | Signal Intensity Old | Young | Gene | Class | CR Prevention |
|---|---|---|---|---|---|---|---|
| M88354 | 5.7 | 1.9 | 165 | −109 | Vasopressin-neurophysin II | Osmotic stress | 68% |
| M17440 | 4.9 | 0.2 | 786 | 141 | Complement C4 | Immune/inflammatory | 52% |
| AA120109 | 4.1 | 0.8 | 278 | 65 | Interferon-induced protein 6–16 homolog | Immune/inflammatory | 100% |
| M88355 | 2.7 | 0.6 | 195 | 70 | Oxytocin-neurophysin | Osmotic stress | 23% |
| AA037945 | 2.5 | 0.2 | 254 | 73 | Beta-SNAP homolog | Transport | N |
| AA162093 | 2.5 | 0.2 | 145 | 21 | Pre-mRNA splicing factor PRP22 | RNA metabolism | N |
| AA137962 | 2.4 | 0.2 | 150 | 39 | RAS-retated protein RAB-14 | Neurotransmitter release | N |
| K01347 | 2.3 | 0.4 | 420 | 178 | Glial fibrilaty acidic protein (GFAP) | Stress response | 38% |
| AA027404 | 2.3 | 0.1 | 129 | −43 | Na/K-transporting ATPase beta-2 chain | Ionic transport | N |
| U60593 | 2.3 | 0.4 | 279 | 131 | Cap43 | Stress response | N |
| AA137871 | 2.3 | 0.6 | 55 | −33 | Phosphatidylinositol-4-phosphate 5-kinase | Signal transduction | N |
| U61751 | 2.3 | 0.2 | 299 | 128 | VAMP-1 | Transport | N |
| M210150 | 2.2 | 0.2 | 209 | 74 | Lysozyme C | Immune/inflammatory | 54% |

TABLE 5-continued

Aging-related increases in gene expression in neocortex of C57BL/6 mice*

| ORF | Δ Age (fold) | SE | Signal Intensity Old | Young | Gene | Class | CR Prevention |
|---|---|---|---|---|---|---|---|
| AA153990 | 2.2 | 0.9 | 343 | 155 | GTP:AMP phosphotransferase mitochondnal | Energy metabolism | 100% |
| W29462 | 2.1 | 0.3 | 114 | −49 | Calpactin I light chain | Structural | N |
| L39123 | 2.1 | 0.2 | 1887 | 768 | Apolipoprotein D (apoD) | Stress response | N |
| U16297 | 2.0 | 0.5 | 124 | 47 | Cytochrome B561 | Transport | N |
| M26251 | 2.0 | 0.3 | 484 | 260 | Vimentin | Stress response | N |
| AA163911 | 2.0 | 0.2 | 130 | 38 | Casein kinase I, delta isoform | Stress response | N |
| AA022006 | 2.0 | 0.2 | 115 | −48 | CD40L receptor precursor | Immune/inflammatory | N |
| AA124859 | 2.0 | 0.2 | 17 | −54 | ICAM-2 | Immune/inflammatory | N |
| Y00305 | 1.9 | 0.2 | 225 | 101 | Potassium channel protein-1 | Transport | N |
| AA116604 | 1.9 | 0.1 | 515 | 272 | Catnepsin Z | Stress response | 70% |
| M95200 | 1.9 | 0.3 | 168 | 92 | Vascular endothelial growth factor | Growth factor | N |
| L16894 | 1.9 | 0.4 | 123 | −71 | Cyclophilin C-AP | Stress response | 100% |
| L20315 | 1.9 | 0.2 | 120 | 66 | MPS1 gene | Immune/inflammatory | N |
| AA028501 | 1.9 | 0.2 | 74 | 16 | Cylochrome c oxidase subunit VIII-H | Energy metabolism | N |
| X86569 | 1.9 | 0.2 | 24 | 31 | LIM-kinase | Unknown | N |
| AA105716 | 1.9 | 0.2 | 107 | 14 | Fructose-1,6-bisphosphatase homolog | Energy metabolism | 87% |
| W13646 | 1.8 | 0.1 | 1278 | 705 | TI.225 (ubiquitin) | Stress response | N |
| J03236 | 1.8 | 0.3 | 681 | 362 | JunB | Stress response | 46% |
| X52886 | 1.8 | 0.1 | 1050 | 555 | Cathepsin D | Stress response | 64% |
| AA028273 | 1.8 | 0.3 | 331 | 153 | Protein phosphatase inhibitor 2 (IPP-2) | Unknown | N |
| X16995 | 1.8 | 0.1 | 757 | 375 | N10 | Steroid metabolism | N |
| X16995 | 1.8 | 0.1 | 624 | 363 | Complement C1q B-chain | Immune/inflammitory | 100% |
| X66295 | 1.8 | 0.1 | 823 | 467 | Complement Ctq C-chain | Immune/inflammitory | 75% |
| U22445 | 1.8 | 0.5 | 201 | 160 | Serine/threonine kinase (Akt2) | Energy metabolism | 100% |
| U17297 | 1.8 | 0.2 | 6 | −43 | Integral membrane phosphoprotein 7.2b | Unknown | N |
| AA059700 | 1.8 | 0.2 | 1467 | 797 | MHC class I B(2)-microglobulin | Immune/inflammitory | 64% |
| L29503 | 1.8 | 0.1 | 192 | 103 | Myelin/oligodendrocyte glycoprotein (0 mg) | Unknown | N |
| AA168918 | 1.8 | 0.4 | 326 | 166 | Na/K-transporting ATPase gamma chain | Transport | N |
| M90364 | 1.8 | 0.1 | 326 | 202 | Beta-catenin | Stress response | N |
| AA061086 | 1.8 | 0.2 | 179 | 89 | Hsp40 | Stress response | 52% |
| W50891 | 1.8 | 0.3 | 41 | −3 | Creatine kinase | Energy metabolism | N |
| W67046 | 1.8 | 0.2 | 105 | 71 | Exodus-2 | Immune/inflammitory | N |
| W13875 | 1.8 | 0.2 | 216 | 125 | Myosin regulatory light chain 2-A | Unknown | N |
| X67083 | 1.8 | 0.3 | 121 | 47 | Chop-10 GADD153 | Stress response | N |
| AA089110 | 1.8 | 0.2 | 23 | −35 | Dynein beta chain, ciliary | Transport | N |
| V00727 | 1.7 | 0.3 | 404 | 236 | c-fos(p55) | Stress response | 100% |
| AA062328 | 1.7 | 0.2 | 113 | 23 | DNAJ protein homolog 2 | Stress response | N |
| AA122619 | 1.7 | 0.3 | 14 | −43 | Set protein (HLA-DR associated protein II) | Unknown | N |
| M73741 | 1.7 | 0.2 | 1313 | 730 | Alpha-B2-crystallin gene | Stress response | 67% |
| X70393 | 1.7 | 0.4 | 146 | 65 | Inter-alpha-inhibitor H3 chain | Immune/inflammatory | 56% |
| AA124698 | 1.7 | 0.7 | 100 | 42 | Lethal(1)discs large-1 | Unknown | N |
| W14434 | 1.7 | 0.2 | 401 | 240 | Fructose-bisphosphate aldolase | Energy metabolism | N |
| W89579 | 1.7 | 0.2 | 83 | −3 | RAS-related protein RAB-4 | Signal transduction | N |
| AA089333 | 1.7 | 0.1 | 336 | 221 | Cathepsin S precursor | Stress response | 56% |
| U19521 | 1.7 | 0.2 | 70 | 31 | Vesicle transport protein (munc-18c) | Transport | N |
| AA107137 | 1.7 | 0.3 | 204 | 118 | Casein kinase I, gamma | Unknown | N |
| M106166 | 1.7 | 0.2 | 2312 | 1372 | Elongation factor 2 (EF-2) homolog | RNA metabolism | N |
| M31811 | 1.7 | 0.1 | 748 | 457 | Clathrin light chain B | Transport | 100% |
| AA140487 | 1.7 | 0.3 | 23 | −25 | Cyclophilin A homolog | Stress response | 100% |
| U37419 | 1.7 | 0.2 | 58 | −29 | G protein alpha subunit (GNA-15) | Signal transduction | N |
| AA114781 | 1.7 | 0.2 | 52 | 26 | Uridylate kinase | DNA metabolism | N |
| X58861 | 1.6 | 0.1 | 1128 | 694 | Complement C1Q alpha-chain | Immune/inflammatory | 100% |
| AA048650 | 1.6 | 0.2 | 169 | 100 | Estradiol 17 β-dehydrogenase 3 homolog | Steroid metabolism | N |
| W46723 | 1.6 | 0.2 | 83 | 46 | Creatine kinase, B chain homolog | Energy metabolism | N |
| U16162 | 1.6 | 0.7 | 112 | 82 | Prolyl 4-hydroxylase alpha(I)-subunit | Structural | N |
| X68273 | 1.6 | 0.2 | 105 | 73 | Macrosialin | Immune/inflammatory | N |
| W48962 | 1.6 | 0.7 | 87 | 38 | β-adrenergic receptor kinase 1 | Signal transduction | N |
| AA063858 | 1.6 | 0.2 | 135 | 80 | RHO-related GTP-binding protein RHOG | Signal transduction | 100% |
| M15525 | 1.6 | 0.1 | 22 | −58 | Laminin B1 | Neuronal outgrowth | N |
| AA068780 | 1.6 | 0.1 | 275 | 187 | Phosphoserine aminotransferase homolog | Unknown | 76% |
| U27462 | 1.6 | 0.3 | 133 | 79 | BS4 peptide | Unknown | N |
| AA106077 | 1.6 | 0.1 | 116 | 64 | Glutathione peroxidase | Stress response | 76% |
| AA119959 | 1.6 | 0.2 | 194 | 128 | Protein transport protein SEC23 | Transport | N |
| AA061170 | 1.6 | 0.2 | 39 | −18 | NEDD-4 protein | Unknown | N |
| X16151 | 1.6 | 0.2 | 93 | 61 | T-lymphocyte activation 1 protein (ETa-1) | Immune/inflammatory | N |
| W29462 | 1.6 | 0.3 | 114 | −49 | Calpactin I light chain (p11) | Unknown | N |
| AA097579 | 1.6 | 0.1 | 24 | −20 | Zinc finger protein 91 homolog | Unknown | 52% |
| X64070 | 1.6 | 0.3 | 252 | 163 | 46kDa mannose 6-phosphate receptor | Lysosomal | N |
| W48519 | 1.6 | 0.2 | 98 | 100 | GTR94 homolog | Stress response | N |
| X78682 | 1.6 | 0.2 | 408 | 269 | B-cell receptor associated protein (BAP) 32 | Unknown | N |
| AA106166 | 1.6 | 0.2 | 2312 | 1372 | Elongation factor 2 homolog | Protein metabolism | N |
| AA169054 | 1.6 | 0.2 | 279 | 184 | GTP-binding protein GTR1 | Signal transduction | N |
| W51181 | 1.6 | 0.3 | 42 | 25 | DNA-directed RNA polymerase II | RNA metabolism | 75% |

TABLE 5-continued

Aging-related increases in gene expression in neocortex of C57BL/6 mice*

| ORF | Δ Age (fold) | SE | Signal Intensity Old | Young | Gene | Class | CR Prevention |
|---|---|---|---|---|---|---|---|
| AA036390 | 1.6 | 0.2 | 146 | 83 | DNA-binding protein inhibitor ID-1 | Transcriptional factor | 75% |
| L08115 | 1.5 | 0.2 | 309 | 236 | Human CD9 antigen homolog | Structural | 100% |
| U37353 | 1.5 | 0.2 | 191 | 121 | Protein phosphatase 2A B'alpha3 regulatory subunit | Signal transduction | N |
| L10244 | 1.5 | 0.2 | 316 | 206 | Spermidine/spermine N1-acetyltransferase | Polyamine metabolism | N |
| J05154 | 1.5 | 0.2 | 72 | 6 | Cholesterol acyltransferase (LCAT) | Steroid metabolism | N |
| D43643 | 1.5 | 0.2 | 62 | 36 | YL-1 | Unknown | N |
| M34141 | 1.5 | 0.1 | 39 | 5 | COX-1 | Immune/inflammatory | 100% |
| L28177 | 1.5 | 0.1 | 35 | −9 | GADD 45 | Stress response | N |
| X85992 | 1.5 | 0.1 | 51 | 10 | Semaphorin C | Neuronal remoldeling | N |
| AA098307 | 1.5 | 0.2 | 85 | 47 | Tubulin beta 5 | Microtubule component | N |

*The values presented for Signal Intensity are the averages of three mice per age group and are expressed as data for old/young mice. The prevention by CR is shown as being none (N) or the calculated percentage effect. The SE was calculated for the nine pair-wise comparisons and was obtained by dividing the standard deviation by the square root of 3. The method from which signal intensity is used to estimate fold changes is described in the Methods section of the manuscript.

TABLE 6

Aging-related decreases in gene expression in neocortex of C57BL/6 mice*

| ORF | Δ Age (fold) | SE | Signal Intensity Old | Young | Gene | Class | CR Prevention |
|---|---|---|---|---|---|---|---|
| X74134 | −3.0 | 1.1 | 157 | 387 | Ovalbumin upstream promoter | Transcriptional factor | N |
| L24430 | −2.7 | 0.6 | 56 | 161 | Osteocalcin precursor | Unknown | N |
| AA124352 | −2.5 | 0.5 | 19 | 274 | Neuromedin B precursor homolog | Neurotransmssion | 54% |
| D31898 | −2.2 | 0.5 | 116 | 253 | Protein tyrosine phosphatase, PTPBR7 | Unknown | N |
| W29468 | −2.2 | 0.3 | 133 | 284 | Myosin tight chain 2 mRNA | Unknown | N |
| AA065993 | −2.2 | 0.3 | 16 | 115 | GTP-binding nuclear protein RAN homolog | Signal transduction | N |
| U35323 | −2.1 | 0.3 | 11 | 135 | H2-M | Unknown | N |
| W98695 | −2.1 | 0.2 | 3 | 120 | Plasma retinol-binding protein precursor | Steroid metabolism | N |
| AA062463 | −2.1 | 0.2 | 63 | 168 | Kidney androgen-regulated protein | Steroid metabolism | N |
| U38196 | −2.1 | 0.6 | 64 | 151 | Palmytoylated protein p55 | Signal transduction | 100% |
| L36135 | −2.1 | 0.3 | −42 | 32 | T cell receptor delta chain, C region | Immune/inflammatory | N |
| D32200 | −2.1 | 0.3 | 38 | 101 | Hes-3 | Unknown | N |
| W98898 | −2.1 | 0.4 | −21 | 125 | Transforming protein RFP | Growth factor | N |
| U29762 | −2.0 | 0.2 | 396 | 744 | Albumin gene D-Box binding protein | Circadian rhythm | N |
| AA138711 | −2.0 | 0.5 | 222 | 321 | Protein kinase C inhibitor protein | Unknown | N |
| W13586 | −2.0 | 0.3 | 135 | 548 | Atrial/fetal isoform myosin alkali light chain | Stuctural | 49% |
| X67812 | −2.0 | 0.3 | 41 | 120 | ret proto-oncogene | Unknown | N |
| M97812 | −2.0 | 0.2 | 12 | 85 | REX-1 | Steroid metabolism | N |
| W11011 | −2.0 | 0.4 | 418 | 673 | NEDD8 | Protein metabolism | N |
| X13538 | −2.0 | 0.2 | 66 | 176 | Hox-1,4 gene | Growth factor | N |
| X66405 | −2.0 | 0.5 | 186 | 330 | Collagen alpha 1 chain type VI | Structural | 100% |
| AA050791 | −2.0 | 0.5 | 194 | 355 | Creatine kinase, M chain | Energy metabolism | N |
| W55515 | −1.9 | 0.4 | 132 | 243 | Cyclic-AMP-dependent ATF-4 | Transcriptional factor | 100% |
| L33416 | −1.9 | 0.3 | 184 | 291 | Clone p85 secreted protein | Unknown | 100% |
| X70398 | −1.9 | 0.9 | 186 | 325 | PTZ-17 | Growth factor | N |
| M84412 | −1.8 | 0.1 | 46 | 128 | Antigen (Ly-9) | Immune/inflammatory | 47% |
| AA067927 | −1.8 | 0.2 | 63 | 132 | DNA-PK-catalytic subunit | DNA metabolism | N |
| Y09585 | −1.8 | 0.4 | 143 | 212 | Serotonin 4L receptor | Neurotransmission | N |
| X95255 | −1.8 | 0.1 | 6 | 72 | Gli3 protein | Growth factor | N |
| U37459 | −1.8 | 0.1 | 37 | 87 | Glial-derived neurotrophic factor (GDNF) | Growth factor | N |
| M99377 | −1.8 | 0.3 | 121 | 270 | Alpha-2 adrenergic receptor | Neurotransmission | N |
| D83585 | −1.8 | 0.5 | 916 | 1457 | Proteasome Z subunit | Protein metabolism | N |
| U52222 | −1.8 | 0.2 | 61 | 160 | Mel-1a melatonin receptor | Neuropeptide | N |
| M13710 | −1.7 | 0.3 | 120 | 219 | Interferon alpha-7 gene | Immune/inflammatory | N |
| D76446 | −1.7 | 0.2 | 103 | 199 | TAK1 | Stress response | N |
| U64445 | −1.7 | 0.2 | 12 | 56 | Ubiquitin fusion-degradation protein (ufd1l) | Protein metabolism | 100% |
| U39545 | −1.7 | 0.3 | 144 | 235 | Bone morphogenetic protein 8B (Bmp8b) | Growth factor | N |
| W59776 | −1.7 | 0.2 | 95 | 174 | Vacuolar ATP synthase catalytic subunit A | pH regulation | N |
| AA071792 | −1.7 | 0.2 | 36 | 89 | GSTP-1 | Protein metabolism | N |
| AA052547 | −1.7 | 0.3 | −2 | 95 | PA-FABP homolog | Unknown | 100% |
| D63819 | −1.7 | 0.2 | 61 | 143 | Neuropeptide Y-Yll receptor | Neuropeptide | N |
| W08326 | −1.7 | 0.2 | 173 | 265 | 51PK(L) homolog | Unknowm | N |
| AA000468 | −1.7 | 0.2 | 113 | 195 | p55CDC | DNA metabolism | 100% |
| U66203 | −1.7 | 0.2 | 111 | 181 | FHF-3 | Growth factor | N |
| AA051632 | −1.7 | 0.2 | 112 | 167 | MEK5 | Signal transduction | 61% |
| AA051147 | −1.7 | 0.2 | 114 | 264 | Chemotaxis protein cheY homolog | Unknown | N |

TABLE 6-continued

Aging-related decreases in gene expression in neocortex of C57BL/6 mice*

| | Δ Age | | Signal Intensity | | | | CR |
|---|---|---|---|---|---|---|---|
| ORF | (fold) | SE | Old | Young | Gene | Class | Prevention |
| X84692 | −1.7 | 0.2 | 24 | 91 | Spnr mRNA for RNA binding protein | DNA metabolism | N |
| U53925 | −1.7 | 0.3 | 100 | 169 | HCF1 | Unknown | 33% |
| AA038142 | −1.7 | 0.3 | 251 | 376 | RCC1 | DNA metabolism | N |
| W54662 | −1.7 | 0.1 | 87 | 188 | Antithrombin-III precursor (ATIII) | Immune/inflammatory | N |
| U13705 | −1.7 | 0.2 | 324 | 494 | Plama glutathione peroxidase (MUSPGPX) | Stress response | 44% |
| X75384 | −1.7 | 0.2 | 91 | 156 | SAX-1 | Growth factor | N |
| Z32767 | −1.7 | 0.3 | 117 | 205 | RAD52 | DNA metabolism | 76% |
| AA107752 | −1.6 | 0.6 | 225 | 336 | Elongationfactor 1-gamma | Protein metabolism | N |
| M12836 | −1.6 | 0.6 | 56 | 116 | T-cell receptor gamma chain gene C-region | Immune/inflammatory | N |
| AA060704 | −1.6 | 0.2 | 975 | 1407 | Glutathione S-transferase MU 5 | Unknown | N |
| AA118294 | −1.6 | 0.1 | 99 | 161 | Vitronectin homolog | Unknown | N |
| AA123026 | −1.6 | 0.1 | 72 | 166 | Pancreatitis-associated protein 3 homolog | Unknown | 100% |
| AA065652 | −1.6 | 0.1 | 39 | 99 | Ubiquitin carboxyl-terminal hydrolase | Protein metabolism | N |
| W46104 | −1.6 | 0.2 | 19 | 58 | DNA-repair protein XP-E | DNA metabolism | N |
| M88694 | −1.6 | 0.2 | 67 | 109 | Thioether S-methyltransferase | Unknown | 57% |
| AA117004 | −1.6 | 0.1 | 6 | 61 | Heat shock cognate 71 KD protein homolog | Stress response | N |
| M15501 | −1.6 | 0.1 | 229 | 325 | Adult cardiac muscle alpha-actin | Stuctural | 100% |
| U49430 | −1.6 | 0.2 | 78 | 108 | Ceruloplasmin | Transport | N |
| X69019 | −1.6 | 0.2 | 36 | 71 | Hox 3.5 gene, complete cds | Growth factor | N |
| M28666 | −1.6 | 0.2 | 317 | 496 | Porphobilinogen deaminase | Biosynthesis | 44% |
| W368759 | −1.6 | 0.1 | 49 | 112 | CMP-N-acetylneuraminate-beta-1,4-galactoside alpha-2,3-sialyltransferase | Sialytransferase | N |
| W11666 | −1.6 | 0.2 | 105 | 207 | apolipoprotein H | Lipid metabolism | N |
| W09925 | −1.6 | 0.1 | 26 | 102 | Endothelial actin-binding protein | Growth factor | 74% |
| AA116282 | −1.6 | 0.1 | 140 | 355 | TNF alpha precursor | Immune/inflammatory | 56% |
| D37791 | −1.6 | 0.0 | 556 | 895 | Beta-1,4,-galactosyltransferase | Unknown | N |
| W12658 | −1.6 | 0.2 | 143 | 216 | FKBP-rapamycin associated protein (FRAP) | Unknown | N |
| Z468454 | −1.6 | 0.2 | −16 | 39 | Preproglucagon | Energy metabolism | N |
| AA103045 | −1.5 | 0.1 | 57 | 106 | Cleavage stimulation factor, 64 Kd subunit | RNA metabolism | N |
| AA108891 | −1.5 | 0.2 | 4 | 62 | Putative ATP-dependent RNA helicase | RNA metabolism | 55% |
| AA153522 | −1.5 | 0.3 | 80 | 159 | Serine/threonine protein kinase sulu | Unknown | N |
| M23501 | −1.5 | 0.2 | 33 | 101 | TCA3 | Unknown | 61% |
| AA063762 | −1.5 | 0.1 | 112 | 193 | Zinc finger protein 36 homolog (KOX18) | Unknown | 63% |
| AA098588 | −1.5 | 0.1 | 84 | 137 | Zinc finger protein HRX (ALL-1) | Unknown | 57% |
| W15873 | −1.5 | 0.2 | 161 | 258 | tctex-1 mRNA | Unknown | 61% |
| AA170748 | −1.5 | 0.1 | −14 | 48 | 40S Ribosomal protein S4 | Unknown | N |
| W80326 | −1.5 | 0.1 | −11 | 86 | Sex-determining protein FEM-1 | Unknown | N |
| AA140159 | −1.5 | 0.2 | 65 | 134 | Thiol-specific antioxidant protein homolog | Stress response | N |
| D16492 | −1.5 | 0.1 | 19 | 58 | RaRF | Unknown | 56% |
| D85845 | −1.5 | 0.2 | 48 | 88 | Atonal homolog-3 | Growth factor | N |
| L06451 | −1.5 | 0.1 | −55 | 87 | Agouti switch protein mRNA | Unknown | 100% |
| AA166500 | −1.5 | 0.2 | 51 | 141 | Transcriptional regulatory protein RPD3 | Unknown | N |
| L28035 | −1.5 | 0.1 | 377 | 578 | Protein kinase C-gamma mRNA | Unknown | 100% |
| U52197 | −1.4 | 0.1 | 296 | 439 | Poly(A) polymerase V | RNA metabolism | N |
| D29763 | −1.4 | 0.1 | 799 | 1130 | Seizure-related, product 6 type 3 precursor | Unknown/response | 50% |
| U22015 | −1.4 | 0.1 | 89 | 130 | Retinoid X receptor interacting protein | Steroid metabolism | 100% |

*The values presented for Signal Intensity are the averages of three mice per age group and are expressed as data for old/young mice. The prevention by CR is shown as being none (N) or the calculated percentage effect. The SE was calculated for the nine pairwise comparisons and was obtained by dividing the standard deviation by the square root of 3. The method from which signal intensity is used to estimate fold changes is described in the Methods section of the manuscript.

TABLE 7

Caloric restriction-related increases in gene expression in neocortex ot C57BL/6 mice*

| | CR | | Signal Intensity | | | |
|---|---|---|---|---|---|---|
| ORF | Increase | SE | CR | Control | Gene | Class |
| J04971 | 4.1 | 0.7 | 410 | 68 | Slow/cardiac troponin C (cTnC) | Unknown |
| D13903 | 3.1 | 1.2 | 150 | 49 | MPTPdelta (type A) | Growth factors |
| M36660 | 3.1 | 0.3 | 24 | −114 | NAD(P)H menadione oxidoreductase | Stress response |
| M55617 | 3.1 | 0.6 | 27 | −48 | MMCP-4 | unknown |
| W65176 | 3.0 | 0.3 | 39 | −35 | BMP-1 | Growth factor |
| AA118682 | 3.0 | 0.6 | 62 | −12 | Trithorax homolog 2 | Transcriptional factor |
| AA014816 | 3.0 | 0.7 | 257 | 38 | Prolactin homolog | Unknown |
| U39904 | 2.9 | 1.4 | 100 | −169 | Citron, putative rho/rac effector | Signal transduction |
| AA061310 | 2.9 | 0.7 | 87 | 29 | Mitochondrial LON protease | Energy metabolism |
| U02098 | 2.8 | 0.5 | 82 | 36 | Pur-alpha | DNA metabolism |
| M29395 | 2.8 | 0.3 | 38 | −20 | Orotidine-5-monophosphate decarboxylase | DNA metabolism |

TABLE 7-continued

Caloric restriction-related increases in gene expression in neocortex ot C57BL/6 mice*

| ORF | CR Increase | SE | Signal Intensity CR | Control | Gene | Class |
|---|---|---|---|---|---|---|
| M23236 | 2.8 | 0.5 | 16 | −57 | Retrovirus POL protein homolog | Unknown |
| M13019 | 2.8 | 0.4 | −15 | −130 | Thymidylate synthase | DNA metabolism |
| X76858 | 2.6 | 0.4 | 58 | −17 | phi AP3 | Unknown |
| W56940 | 2.5 | 0.2 | 81 | 24 | Neuronal-glial cell adhesion molecule homolog | Unknown |
| X59846 | 2.4 | 0.6 | 215 | 156 | GAS 6 | Growth factor |
| U05247 | 2.4 | 0.3 | 666 | 250 | c-Src kinase | Signal transduction |
| AA104316 | 2.3 | 0.3 | 25 | −46 | Type-I ER resident kinase PERK | Stress response |
| L04302 | 2.3 | 0.2 | 49 | 2 | Thrombospondin 3 | Structural |
| W55507 | 2.3 | 0.3 | 31 | −14 | D(2) Dopaimne receptor | Neurotransmission |
| AA014909 | 2.3 | 0.4 | 56 | −39 | Gastrula zinc finger protein XLCGF20.1 | Unknown |
| U46923 | 2.2 | 0.8 | 71 | −13 | G protein-coupled receptor GPR19 | Unknown |
| M34857 | 2.2 | 0.1 | 176 | 57 | Hox-2.5 | Growth factor |
| M74227 | 2.2 | 0.3 | 162 | 48 | Cyclophilin C (cyp C) | Immune/inflammttory |
| W12794 | 2.2 | 0.3 | 48 | −59 | Transforming protein MAF homolog | Transcriptional factor |
| X62940 | 2.2 | 0.1 | 2199 | 931 | TSC-22 | Unknown |
| L06451 | 2.2 | 0.1 | 136 | −55 | Agouti switch protein | Unknown |
| AA052547 | 2.2 | 0.1 | 74 | −2 | Fatty acid-binding protein, epidermal (E-FABP) | Transport |
| W17956 | 2.2 | 0.4 | 106 | −2 | Zinc finger protein 42 homolog | Unknown |
| X95226 | 2.2 | 0.4 | 53 | −1 | Dystrobrevin | Structural |
| AA152808 | 2.2 | 0.2 | 141 | 24 | Proteine kinase PASK | Signal transduction |
| AA014512 | 2.1 | 0.5 | 32 | −3 | Unknown | Unknown |
| W74811 | 2.1 | 0.4 | 17 | −46 | Apolipoprotein c-II precursor (APO-CII) | Transport |
| U69270 | 2.1 | 0.7 | 323 | 210 | LIM domain binding protein 1 (Ldb1) | Growth factor |
| W54720 | 2.1 | 0.2 | 100 | 19 | CaII-transporting ATPase (brain isoform 1) | Unknown |
| X13460 | 2.1 | 0.1 | 313 | 151 | Annexin VI | Signal transduction |
| U61362 | 2.1 | 0.3 | 57 | −35 | Groucho-related gene 1 protein (Grg1) | Unknown |
| W09323 | 2.1 | 0.3 | 91 | −11 | Endothelin-2 precursor(ET-2) | Unknown |
| W70403 | 2.1 | 0.2 | 17 | −19 | mafF | Unknown |
| AA071685 | 2.0 | 0.4 | 93 | 47 | Elongation factor 1-alpha chain homolog | Protein metabolism |
| W14673 | 2.0 | 0.4 | 133 | 8 | BAT3 | Unknown |
| W53409 | 2.0 | 0.3 | 33 | −28 | Protein kinase C homolog, alpha type | Signal transduction |
| U19880 | 2.0 | 0.1 | 26 | −6 | D4 dopamine receptor gene | Neurotransmission |
| M75875 | 2.0 | 0.4 | 280 | 119 | MHC H2-K homolog | Unknown |
| W62842 | 2.0 | 0.2 | 12 | −24 | ATP synthase lipid-binding protein P2 precursor | Energy metabolism |
| U48397 | 2.0 | 0.3 | 126 | 40 | Aquaporin 4 | Osmotic stress |
| J00475 | 2.0 | 0.3 | 74 | −34 | Ig alpha chain region C | Immune/inflammatory |
| M57960 | 2.0 | 0.2 | 21 | −18 | Carboxylesterase | Unknown |
| X57800 | 2.0 | 0.1 | 560 | 274 | PCNA | DNA metabolism |
| U36277 | 2.0 | 0.3 | 123 | 70 | 1-kappa β alpha chain | Stress response |
| AA015291 | 2.0 | 0.3 | 340 | 67 | Probable E1–E2 ATPase | Unknown |
| W82109 | 2.0 | 0.3 | 23 | 29 | Kinesin light chain (KLC) | Transport |
| M83380 | 1.9 | 0.2 | 25 | −26 | Rel B | Immune/inflammatory |
| U13174 | 1.9 | 0.2 | 36 | 2 | Basolateral Na-K-2Cl cotransponer | Transport |
| M33960 | 1.9 | 0.2 | 19 | 1 | Plasminogen actvator inhibitor (PAI-1) | Growth factor |
| X72310 | 1.9 | 0.3 | 106 | 38 | DRTF-polypeptide-1 (DP-1) | Transcriptional factor |
| AA059886 | 1.9 | 0.2 | 8 | −52 | Retinal degeneration C protein | Apaptotic factor |
| U02278 | 1.9 | 0.2 | 18 | −32 | Hox-B3 | Growth factor |
| AA072842 | 1.9 | 0.2 | 126 | 72 | Na⁺ and Cl⁻ dependent transporter NTT73 | Transport |
| M98339 | 1.9 | 0.2 | 113 | −15 | GATA-4 | Transcriptional factor |
| W13427 | 1.9 | 0.3 | 195 | 94 | Platelet factor 4 precusor | Unknown |
| U44955 | 1.9 | 0.2 | 45 | 2 | Alpha3 connexin gene | Transport |
| L24191 | 1.9 | 0.1 | 104 | 25 | Intrinsic factor | Transport |
| W08109 | 1.9 | 0.3 | 142 | 99 | Protein kinase C inhibitor 1 (PKC-1) homolog | Unknown |
| W36570 | 1.9 | 0.3 | 146 | 67 | DNA mismatch repair protein MSH2 | DNA metabolism |
| Z34524 | 1.8 | 0.2 | 42 | −20 | Protein kinase D | Signal transduction |
| AA105081 | 1.8 | 0.2 | 46 | −1 | Initiation factor IF-2, mitochondrial | Protein metabolism |
| U18797 | 1.8 | 0.2 | 95 | −3 | MHC class I antigen H-2M3 | Unknown |
| M11988 | 1.8 | 0.3 | 141 | 82 | Hox-A6 | Growth factor |
| U17961 | 1.8 | 0.2 | 123 | 81 | p62 ras-GAP associated phosphoprotein | Signal transduction |
| W85103 | 1.8 | 0.1 | 24 | −17 | IGF binding protein 4 precursor homolog | Energey metabolism |
| X07997 | 1.8 | 0.2 | 230 | 128 | MHC class I T-cell antigen Lyt3.1 | Immune/inflammatory |
| W46723 | 1.8 | 0.3 | 164 | 83 | Creatine kinase, B chain homolog | Unknown |
| W48464 | 1.8 | 0.4 | 18 | −7 | Protein-tyrosine phosphatase MEG2 homolog | Unknown |
| L06322 | 1.8 | 0.1 | 84 | −4 | Delta opioid receptor | Neurotransmission |
| W49178 | 1.8 | 0.1 | 605 | 508 | Tubulin beta-1 chain homolog | Structural |
| W48477 | 1.8 | 0.2 | 106 | 61 | Thyrotroph embryonic factor homolog | Unknown |
| W64225 | 1.8 | 0.3 | 80 | 44 | G21 | Unknown |
| L28167 | 1.8 | 0.2 | 88 | 45 | Zinc finger protein | Unknown |
| W97199 | 1.8 | 0.3 | 37 | 62 | Negative regulator of transcription subunit 2 | Transcriptional factor |
| X01971 | 1.8 | 0.2 | 20 | −35 | Interferon alpha 5 (Mu IFN-alpha 5) | Immune/inflammatory |
| AA061266 | 1.8 | 0.3 | 164 | 125 | Oxysterol-binding protein homolog | Transtport |
| U21855 | 1.8 | 0.3 | 94 | 31 | CAF1 | Transcriptional factor |
| W87078 | 1.8 | 0.1 | 182 | 90 | Unknown | Unknown |

TABLE 7-continued

Caloric restriction-related increases in gene expression in neocortex ot C57BL/6 mice*

| ORF | CR Increase | SE | Signal Intensity CR | Control | Gene | Class |
|---|---|---|---|---|---|---|
| W34687 | 1.8 | 0.3 | 188 | 105 | Actin alpha skeletal muscle homolog | Structural |
| K01238 | 1.8 | 0.3 | 191 | 127 | Interferon alpha 2 | Immune/inflammatory |
| U15635 | 1.8 | 0.2 | 70 | 9 | IFN-gamma induced (Mg11) | Unknown |
| L13968 | 1.8 | 0.1 | 98 | 26 | UCR-motif DNA-binding protein | Transcriptional factor |
| M86567 | 1.8 | 0.2 | 122 | 60 | GABA-A receptor alpha-2 subunit | Neurotransmission |
| M87861 | 1.8 | 0.3 | 51 | −22 | Granule membrane protein 140 | Structural |
| W55350 | 1.8 | 0.3 | 14 | −4 | Phosphatidylinositol transfer protein β isoform | Unknown |
| L43567 | 1.8 | 0.1 | 35 | −21 | B-cell receptor gene | Immune/inflammatory |
| AA153196 | 1.8 | 0.2 | 55 | −19 | Ubiquilin-activating enzyme E1 homolog | Protein metabolism |
| M28312 | 1.8 | 0.1 | 109 | 41 | Metalloprotease inhibtor TIMP 1 | Immune/inflammatory |

*The values presented for Signal Intensity are the averages of three mice per age group and are expressed as data for old CR/old control mice. The SE was calculated for the nine pairwise comparisons and was obtained by dividing the standard deviation by the square root of 3. The method from which signal intensity is used to estimate fold changes is described in the Methods section of the manuscript.

TABLE 8

Caloric restriction-related decreases in gene expression in neocortex ot C57BL/6 mice*

| ORF | CR Increase | SE | Signal Intensity CR | Control | Gene | Class |
|---|---|---|---|---|---|---|
| X76505 | −7.2 | 1.0 | −195 | 73 | Tyro 10 | Signal transduction |
| U43088 | −6.3 | 1.1 | −109 | 164 | IL-17 (CTLA-8) | Immune/inflammatory |
| W50186 | −5.6 | 2.1 | −38 | 129 | Heavy chain homolog | Unknown |
| Y07711 | −3.5 | 0.5 | 28 | 151 | Zyxin | Signal transduction |
| Z47205 | −3.1 | 0.8 | 45 | 200 | PLZF | Transcriptional factor |
| AA000203 | −2.8 | 0.7 | −93 | 26 | Corticosteroid-binding globulin precursor | Transport |
| W83658 | −2.6 | 0.5 | 51 | 197 | Guanine nucleotide-binding protein G(I)/G(S)/G(O) homolog | Signal transduction |
| L46815 | −2.6 | 0.2 | 8 | 67 | Ig kappa chain recombination and transcription enhancer | DNA metabolism |
| AA153484 | −2.4 | 0.5 | 208 | 456 | SERCA2 | Ion transport |
| W51466 | −2.4 | 0.4 | 12 | 147 | Chlorine channel protein P64 homolog | Unknown |
| U27398 | −2.4 | 0.4 | 39 | 132 | XPC | DNA Metabolism |
| X58069 | −2.2 | 0.7 | 54 | 164 | H2A.X | DNA metabolism |
| U50712 | −2.2 | 0.4 | 54 | 156 | MCP-5 | Immune/inflammatory |
| M61909 | −2.1 | 0.3 | 39 | 125 | NF-kappa-B p65 | Stress response |
| AA072643 | −2.1 | 0.4 | 49 | 110 | Midkine precursor homolog | Stress response |
| L01991 | −2.1 | 0.3 | 48 | 132 | PANG | Unknown |
| L04678 | −2.1 | 0.2 | −64 | 138 | Integrin beta 4 subunit | Structural |
| W64628 | −2.1 | 0.4 | 62 | 197 | Guanine nucleotide-binding protein G(I)/G(S)/G(O) gamma-7 subunit | Signal transduction |
| X54098 | −2.0 | 0.3 | 55 | 136 | lamin B2 | Structural |
| AA023458 | −2.0 | 0.3 | 20 | 107 | Heat shock 27 KD protein homolog | Stress response |
| D63380 | −2.0 | 0.2 | −19 | 32 | Alpha-1,3-fucosyltransferase | Protein metabolism |
| U15548 | −2.0 | 0.3 | −30 | 42 | Beta 2 thyroid hormone receptor | Energey metabolism |
| AA123385 | −2.0 | 0.2 | 57 | 117 | Phosphorylase B kinase gamma catalytic chain | Energey metabolism |
| X57349 | −2.0 | 0.4 | −10 | 49 | Transferrin receptor | Transport |
| D00659 | −2.0 | 0.1 | 1 | 35 | Aromatase P450 | Biosynthesis |
| AA028875 | −2.0 | 0.2 | −32 | 54 | Glycine-rich cell wall structural homolog | Lysosomal |
| X76291 | −2.0 | 0.1 | 11 | 79 | Ihh (Indian Hedgehog) | Signal transduction |
| AA041982 | −1.9 | 0.3 | 44 | 84 | LARK | Circadian regulation |
| AA118758 | −1.9 | 0.2 | 103 | 206 | Multifunctional aminoacyl-tRNA-synthetase | Protein synthesis |
| W75353 | −1.9 | 0.3 | 90 | 162 | Apolipoprotein C-IV | Transport |
| W55410 | −1.9 | 0.2 | 30 | 111 | Tubulin gamma chain homolog | Unknown |
| L20343 | −1.9 | 0.2 | 22 | 102 | L-type calcium channel beta 2a subunit isoform | Transport |
| W91095 | −1.9 | 0.5 | 44 | 93 | Valyl-tRNA synthetase | Protein metabolism |
| X81593 | −1.9 | 0.1 | 53 | 119 | Winged-helix domain | Transcriptional factor |
| M38248 | −1.9 | 0.2 | −6 | 25 | BALB8N | Unknown |
| J04694 | −1.9 | 0.3 | 48 | 134 | Alpha-1 type IV collagen | Structural |
| L47650 | −1.8 | 0.3 | 50 | 85 | STAT6 R | Immune/inflammatory |
| AA023595 | −1.8 | 0.1 | 38 | 133 | Frizzled protein precursor | Signal transduction |
| AA015168 | −1.8 | 0.2 | 42 | 97 | Interferon-gamma receptor beta chain homolog | Immune/inflammatory |
| AA013951 | −1.8 | 0.1 | 32 | 38 | Creatine transporter homolog | Energey metabolism |
| W78443 | −1.8 | 0.2 | 17 | 106 | MKP-X | Signal transduction |
| D31842 | −1.8 | 0.2 | 66 | 126 | PTP36 | Structural |
| W50138 | −1.8 | 0.2 | 1 | 162 | Putative serine/threonine-protein kinase B0464.5 | Unknown |
| L35307 | −1.8 | 0.2 | 33 | 104 | c-Knox | Transcriptional factor |

TABLE 8-continued

Caloric restriction-related decreases in gene expression in neocortex ot C57BL/6 mice*

| ORF | CR Increase | SE | Signal Intensity CR | Control | Gene | Class |
|---|---|---|---|---|---|---|
| AA073154 | −1.8 | 0.3 | 31 | 68 | Alpha-catenin homolog | Structural |
| W12720 | −1.8 | 0.3 | 149 | 251 | RAP-2B homolog | Signal transduction |
| AA170169 | −1.8 | 0.2 | −17 | 37 | Elongation factor 1-gamma homolog | Protein metabolism |
| W48951 | −1.8 | 0.3 | 8 | 30 | Voltage-dependent anion-selective channel protein 2 homolog | Unknown |
| M35732 | −1.8 | 0.3 | −13 | 17 | Seminal vesicle secretory protein IV | Unknown |
| AA145515 | −1.8 | 0.3 | 68 | 187 | Pre-MRNA splicing factor PRP6 | RNA metabolism |
| W13162 | −1.8 | 0.1 | −7 | 62 | Cell division protein kinase 4 | DNA metabolism |
| J03482 | −1.8 | 0.2 | 42 | 113 | Histone H1 | DNA metabolism |
| W82793 | −1.8 | 0.1 | −4 | 59 | Topoisomerase E III homolog | DNA metabolism |
| Z31360 | −1.8 | 0.3 | 1 | 51 | P/L01 | Unknown |
| Y09632 | −1.8 | 0.1 | 16 | 37 | Rabkinesin-6 | Transport |
| AA066621 | −1.8 | 0.2 | 13 | 63 | 60S ribosomal protein L10 | Protein metabolism |
| U67874 | −1.8 | 0.3 | 46 | 85 | Ubiquitin thiolesterase family | Protein metabolism |
| AA109714 | −1.8 | 0.3 | 562 | 968 | SKP1 | RNA metabolism |
| AA007957 | −1.8 | 0.2 | 210 | 357 | Threonyl-tRNA synthetase homolog | Protein metabolism |
| AA162633 | −1.8 | 0.2 | 46 | 95 | Isoleucyl-tRNA synthetase | Protein metabolism |
| M17299 | −1.8 | 0.3 | 29 | 101 | Phosphoglycerate kinase (pgk-2) | Energy metabolism |
| AA050102 | −1.7 | 0.3 | 211 | 263 | Elongation factor 2 (EF-2) | Protein metabolism |
| W54637 | −1.7 | 0.2 | 72 | 37 | Tubulin beta-2 chain class-II homolog | Unknown |
| D10028 | −1.7 | 0.3 | 167 | 312 | Glutamate receptor channel subunit zeta 1 | Neurotransmission |
| M28587 | −1.7 | 0.2 | −52 | 30 | Alpha leukocyte interferon | Immune/inflammatory |
| AA023506 | −1.7 | 0.2 | 60 | 144 | Insulin receptor substrate-3 | Energey metabolism |
| W70629 | −1.7 | 0.3 | 92 | 158 | COP-II | Protein metabolism |
| U33626 | −1.7 | 0.3 | 66 | 125 | PML isoform 1 (Pml) | Unknown |
| AA144746 | −1.7 | 0.2 | 42 | 92 | EF-1-delta | Protein metabolism |
| M19380 | −1.7 | 0.3 | 1406 | 2303 | Calmodulin (Cam III) | Signal transduction |
| AA144136 | −1.7 | 0.2 | 43 | 100 | Choline kinase Rt homolog | Biosynthesis |
| AA165847 | −1.7 | 0.3 | 331 | 509 | EF-1-alpha2 homolog | Protein metabolism |
| W33415 | −1.7 | 0.2 | 90 | 136 | ATP citrate-lyase | Unknown |
| U35233 | −1.6 | 0.1 | 71 | 109 | Endothelin-1 | Vasoconstrictive peptide |
| W57384 | −1.9 | 0.3 | 6 | 15 | ATP synthase A chain homolog | Energey metabolism |
| X60452 | −1.6 | 0.3 | 124 | 200 | Cytochrome P-450IIIA | Stress response |
| AA02227 | −1.6 | 0.1 | 172 | 279 | Vascular endothlial growth factor | Unknown |
| AA168841 | −1.6 | 0.2 | 169 | 289 | Serine/threonine-protein kinase PAK | Unknown |
| AA120586 | −1.6 | 0.1 | 9 | 64 | Apolipoprotein B-100 precursor | Stress response |
| AA104561 | −1.6 | 0.2 | 104 | 166 | EIF-4A homolog | Protein metabolism |
| X17071 | −1.6 | 0.1 | 25 | 90 | Trophoblast-specific protein | Growth factor |
| M96265 | −1.6 | 0.1 | 153 | 250 | Galactose-1-phosphate uridyl transferase | Biosynthesis |
| AA145160 | −1.6 | 0.2 | 178 | 287 | Translational initiation factor 2 alpha | Protein metabolism |
| X63473 | −1.6 | 0.1 | 69 | 110 | m4 muscannic acetylcholine receptor | Neurotransmission |
| AA002750 | −1.5 | 0.2 | 176 | 290 | 5-lipoxygenase activating protein (FLAP) | Immune/inflammatory |
| W64698 | −1.5 | 0.2 | 51 | 63 | Protein kinase C inhibitor 1 | Signal transduction |
| U63841 | −1.5 | 0.1 | 120 | 197 | NeuroD3 | Growth factors |
| U04294 | −1.5 | 0.1 | 99 | 150 | Potassium channel subunit (m-eag) | Transport |
| M33227 | −1.5 | 0.2 | 259 | 396 | Cryptdin-related (CRS4C) | Immune/inflammatory |
| U20532 | −1.5 | 0.1 | 45 | 67 | P45 NF-E2 related factor 2 (Nrf2) | Transcriptional factor |
| AA140026 | −1.5 | 0.1 | 378 | 519 | DNA directed RNA polymerase polypeptide G | DNA metabolism |
| W09025 | −1.5 | 0.1 | 47 | 68 | ATP synthase B chain homolog | Energey metabolism |
| W29163 | −1.5 | 0.1 | 342 | 465 | Leydig cell tumor 10kd protein homolog | Unknown |
| AA155191 | −1.5 | 0.1 | 36 | 65 | Kinesin heavy chain | Transport |
| M80363 | −1.5 | 0.1 | 63 | 96 | Rep-3 | DNA metabolism |
| AA044561 | −1.4 | 0.2 | 93 | 132 | PEP carboxykinase - mitochondrial | Energey metabolism |
| AA096843 | −1.4 | 0.2 | 130 | 175 | Unknown | Unknown |
| X57277 | −1.4 | 0.1 | 908 | 1298 | Rac 1 | Signal transduction |
| W82998 | −1.4 | 0.1 | 256 | 363 | BUB3 | DNA metabolism |

*The values presented for Signal Intensity are the averages of three mice per age group and are expressed as data for old CR/old control mice. The SE was calculated for the nine pairwise comparisons and was obtained by dividing the standard deviation by the square root of 3. The method from which signal intensity is used to estimate fold changes is described in the Methods section of the manuscript.

TABLE 9

Aging-related increases in gene expression in the cerebellum of C57B/6 mice*

| ORF | Fold Change | SE | Signal Intensity Old | Young | Gene | Class | CR Prevention |
|---|---|---|---|---|---|---|---|
| AA120109 | 9.3 | 3.4 | 254 | 29 | Interferon-induced protein 6–16 precursor | Immune/inflammatory | N |
| M21050 | 6.4 | 0.9 | 291 | 14 | Lysozyme P (Lzp-s) | Immune | 88 |
| X56824 | 5.7 | 1.9 | 160 | 89 | Tumor-induced 32 kD protein (p32) | Unknown | 100 |
| V00727 | 5.6 | 2.6 | 282 | 57 | c-fos | Stress | 30 |
| M13019 | 4.9 | 0.7 | 109 | 3 | Thymidylate synthase | DNA metabolism | 87 |
| L16894 | 4.7 | 1.0 | 192 | 5 | Cyclophilin C (CyCAP) | Immune/inflammatory | N |
| AA146437 | 4.7 | 0.3 | 841 | 169 | Cathepsin S precursor | Stress | 62 |
| X58861 | 4.4 | 0.2 | 719 | 160 | C1Q alpha-chain | Immune/inflammatory | 80 |
| W67046 | 4.3 | 0.8 | 50 | 1 | C6 chemokine | Immune/inflammatory | N |
| X66295 | 4.1 | 0.6 | 508 | 147 | C1q C-chain | Immune/inflammatory | 56 |
| W65899 | 4.1 | 1.8 | 152 | 58 | Guanine nucleotide-binding protein | Signal transduction | 80 |
| U00677 | 4.1 | 2.2 | 16 | −10 | Syntrophin-1 | Neurotransmission | 100 |
| X68273 | 3.9 | 1.8 | 108 | −37 | Macrosialin | Immune/inflammatory | N |
| U19854 | 3.9 | 0.5 | 35 | −63 | Ubiquitinating enzyme E2-20K | Protein metabolism | 100 |
| U63133 | 3.9 | 1.1 | 318 | 95 | Emv-3 | Viral | N |
| L20315 | 3.8 | 0.1 | 97 | 26 | MPS1 | Immune/inflammatory | 56 |
| K01347 | 3.8 | 0.7 | 337 | 109 | Glial fibrillary acidic protein (GFAP) | Stress | 61 |
| M17440 | 3.7 | 0.3 | 445 | 116 | Sex-limited protein (SlpA) | Immune/inflammatory | N |
| X91144 | 3.6 | 1.3 | 38 | −2 | P-selectin glycopratetn ligand 1 | Immune/inflammatory | 100 |
| U43084 | 3.5 | 0.8 | 54 | 18 | IFIT-2 Glucocorticoid-attenuated response | Immune/inflammatory | N |
| AA089333 | 3.4 | 0.2 | 208 | 61 | Cathepsin S precursor | Stress | 71 |
| X83733 | 3.4 | 0.3 | 71 | −7 | SAP62-AMH | RNA metabolism | 100 |
| W45750 | 3.3 | 1.3 | 197 | 257 | Guanine nucleotide-binding protein G(T) | Signal transduction | 100 |
| M22531 | 3.3 | 0.2 | 431 | 146 | C1q B-chain | Immune/inflammatory | 65 |
| AA031244 | 3.1 | 0.4 | 83 | 9 | DNAJ protein homolog HSJ1 | Stress | 100 |
| M60429 | 3.1 | 0.8 | 121 | 37 | Ig-gamma 1 chain | Immune/inflammatory | 100 |
| AA036067 | 3.0 | 0.4 | 815 | 311 | Apolipoprotein E precursor (APO-E) | Lipid transport | 28 |
| U06119 | 2.9 | 0.3 | 27 | 4 | Cathepsin H prepropeptide (ctsH) | Stress response | 55 |
| AA106347 | 2.9 | 0.3 | 243 | 57 | Angiotensinogen precursor | Osmoregulation | 80 |
| W98998 | 2.9 | 0.7 | 182 | 79 | Neurogenic locus notch homolog protein 1 | Immune/inflammatory | 100 |
| AA059700 | 2.8 | 0.3 | 2013 | 687 | MHC class 1 B(2)-microglobulin | Immune/inflammatory | 45 |
| U73037 | 2.8 | 0.8 | 69 | 41 | Interferon regulatory factor 7 (mirf7) | Immune/inflammatory | 50 |
| Y00964 | 2.8 | 0.3 | 780 | 316 | beta-hexosaminidase (Hexb) | Unknown | 47 |
| X55315 | 2.8 | 0.6 | 63 | 15 | Fetus cerebral cortex for 3UTR | Transcription factor | 100 |
| U37465 | 2.8 | 0.1 | 15 | −7 | Protein tyrosine phosphatase phi (PTPphi) | Unknown | 63 |
| L07803 | 2.7 | 1.2 | 24 | −15 | trombospondin 2 | Structural | N |
| U19119 | 2.7 | 0.3 | 52 | −5 | G-proten-like LRG-47 | Immune/inflammatory | N |
| X52886 | 2.6 | 0.2 | 893 | 326 | Cathepsin D | Stress response | 38 |
| W70578 | 2.6 | 1.2 | 31 | 7 | Antigen WC1.1 | Immune/inflammatory | 81 |
| X16705 | 2.6 | 0.4 | 93 | −4 | Laminin B1 | Structural | 84 |
| W57539 | 2.6 | 0.3 | 28 | 6 | Oocyte zinc finger protein XLCOF8 | Unknown | N |
| X52308 | 2.6 | 0.4 | 32 | 9 | Thrombin | Fibrinogen activation | 91 |
| U70859 | 2.6 | 0.7 | 109 | 46 | Cationic amino acid transporter (CAT3) | AA transport | 49 |
| U41497 | 2.6 | 1.1 | 160 | 40 | Very-long chain acyl-CoA dehydrogenase | Lipid metabolism | 100 |
| AA089339 | 2.6 | 0.5 | 76 | 31 | Cystatin C precursor | Immune/inflammatory | 100 |
| X16151 | 2.5 | 0.1 | 239 | 95 | Early T-lymphocyte activation 1 protein | Immune/inflammatory | 49 |
| U37419 | 2.5 | 0.5 | 111 | −2 | G protein alpha subunit (GNA-15) | Unknown | N |
| K02785 | 2.5 | 0.5 | 15 | −6 | r-tos | Stress response | N |
| M12289 | 2.5 | 0.5 | 39 | 25 | Pennatal skeletal myosin heavy chain | Structural | 100 |
| X58849 | 2.4 | 0.4 | 59 | 13 | Murine Hox-4.7 | Developmental | 100 |
| AA063858 | 2.4 | 0.2 | 89 | 32 | Rho-related GTP-binding protein RHOG | Signal transduction | 74 |
| D10632 | 2.4 | 0.2 | 33 | −27 | Zinc finger protein | Transcription factor | N |
| U33005 | 2.3 | 0.4 | 35 | −8 | tbc 1 | Unknown | N |
| W85160 | 2.3 | 0.7 | 70 | 41 | 40S ribosomal protein S4.X isoform | Unknown | 100 |
| U57331 | 2.3 | 1.0 | 42 | 15 | Transcription factor Tbx6 (tbx6) | Developmental | 92 |
| U44731 | 2.3 | 0.2 | 71 | 20 | Putative purine nucleotide binding protein | Immune/inflammatory | N |
| W87253 | 2.3 | 0.6 | 58 | 16 | Integrin beta-5 subunit precursor | Cell adhesion | 100 |
| U53142 | 2.3 | 0.2 | 223 | 101 | Endothelial constitutive nitric oxide syntnase | Neurotransmission | N |
| AA087715 | 2.3 | 0.1 | 85 | −61 | GTPase-activating protein SPA-1 | Unknown | N |
| D49429 | 2.3 | 0.3 | 554 | 251 | Rad21 homolog | DNA metabolism | 73 |
| AA155318 | 2.3 | 0.4 | 291 | 129 | HNRP1 | RNA metabolism | N |
| AA032593 | 2.3 | 0.1 | 99 | 17 | Transducin beta chain 2 | Signal transduction | 83 |
| X03690 | 2.3 | 0.2 | 45 | −13 | Ig mu chain | Immune/inflammatory | 93 |
| M26417 | 2.3 | 0.5 | 54 | 28 | T cell receptor beta chain | Immune/inflammatory | 100 |
| X86374 | 2.2 | 0.6 | 73 | 38 | TAG7 | Immune/inflammatory | 38 |
| W90894 | 2.1 | 0.3 | 27 | −11 | Cell division protein kinase 4 | DNA metabolism | 100 |
| M84005 | 2.2 | 0.7 | 83 | 51 | Olfactory receptor 15 | Odor receptor | 23 |
| X55573 | 2.2 | 0.5 | 55 | 19 | Brain-derived neurotrophic factor | Growth factor | N |
| W30129 | 2.2 | 0.3 | 90 | −16 | Phosphatidylinositol glycan homolog | Structural | 100 |
| AA163771 | 2.2 | 0.3 | 153 | 67 | EIF-2B epsilon subunit | Protein metabolism | N |
| X72910 | 2.1 | 0.4 | 96 | 44 | HSA-C | Unknown | N |
| AA116604 | 2.1 | 0.2 | 303 | 181 | Cathepsin Z | Stress response | 64 |
| L16462 | 2.1 | 0.4 | 51 | 4 | BCL2-related protein A1 | Apoptosis | 58 |

TABLE 9-continued

Aging-related increases in gene expression in the cerebellum of C57B/6 mice*

| ORF | Fold Change | SE | Signal Intensity Old | Young | Gene | Class | CR Prevention |
|---|---|---|---|---|---|---|---|
| L13732 | 2.1 | 0.4 | 53 | 29 | Natl. resistanc-asstd. macrophage protein 1 | Immune/inflammatory | 85 |
| D37791 | 2.1 | 0.1 | 934 | 424 | Beta-1,4-galactosyltransferase | Protein metabolism | 82 |
| AA125097 | 2.0 | 0.1 | 618 | 313 | Unknown | Unknown | 94 |
| AA109998 | 2.0 | 0.2 | 40 | 12 | Hexokinase D homolog | Energy metabolism | 100 |
| M88127 | 2.0 | 0.2 | 33 | −8 | APC2 homolog | Unknown | 82 |
| X13538 | 2.0 | 0.5 | 114 | 45 | Hox-1,4 | Growth/development | 100 |
| V01527 | 2.0 | 0.5 | 28 | 10 | H2-IA-beta | Immune/inflammatory | 100 |
| AA144411 | 2.0 | 0.1 | 86 | 79 | Unknown | Unknown | 100 |
| X63535 | 2.0 | 0.1 | 55 | 21 | Tyrosine-protein kinase receptor UFO | Signal transduction | N |
| M83348 | 2.0 | 0.1 | 42 | 22 | Pregnancy specific glycoprotein homolog | Unknown | N |
| W08211 | 2.0 | 0.2 | 62 | 26 | TGF-beta receptor type III | Signal transdtuction | 100 |
| W13136 | 2.0 | 0.4 | 266 | 87 | Angiotenisinogen | Osmoregulation | 36 |
| W46084 | 2.0 | 0.1 | 89 | 45 | Unknown | Unknown | N |
| U73744 | 2.0 | 0.1 | 3958 | 2909 | Heat shock 70 | Stress response | 100 |
| D29763 | 1.9 | 0.2 | 465 | 271 | Seizure-related, product 6 type 3 | Unknown | 47 |
| AA118121 | 1.9 | 1.0 | 51 | 37 | Isoleucyl-tRNA synthetase | Protein metabolism | N |
| M27034 | 1.9 | 0.2 | 258 | 163 | MHC ctass 1 D-region | Immune/inflammatory | N |
| U35249 | 1.9 | 0.1 | 68 | 36 | CDK-activating kinase assembly factor | DNA metabolism | 61 |
| J03776 | 1.9 | 0.4 | 37 | 22 | Down regulatory protein (rpt-1r) of IL-2 receptor | Immune/inflammatory | N |
| U28728 | 1.9 | 0.3 | 221 | 112 | Els | Signal transduction | 66 |
| AA124192 | 1.9 | 0.2 | 411 | 244 | Unknown | Unknown | 44 |
| W63809 | 1.8 | 0.4 | 136 | 80 | Unknown | Unknown | 73 |
| X16834 | 1.8 | 0.2 | 455 | 182 | Galectin-3 | Immune/inflammatory | N |
| X16995 | 1.8 | 0.2 | 351 | 221 | N10 nuclear hormonal receptor homolog | Unknown | 100 |
| J02870 | 1.8 | 0.2 | 848 | 380 | 40S ribosomal protein SA | Protein metabolism | 100 |
| L21768 | 1.8 | 0.2 | 153 | 76 | EGF 15 | Growth factor | 68 |
| AA117284 | 1.8 | 0.1 | 217 | 123 | Zinc finger protein homolog | Unknown | N |

*The values presented for Signal Intensity are the averages of three mice per age group and are expressed as data for old/young mice. The prevention by CR is shown as being none (N) or the calculated percentage effect. The SE was calculated for the nine pairwise comparisons and was obtained by dividing the standard deviation by the square root of 3. The method which signal intensity is used to estimate fold changes is described in the Methods section of the manuscript.

TABLE 10

Aging-related decreases in gene expression in the cerebellum of C57B/6 mice*

| ORF | Fold Change | SE | Signal Intensity Old | Young | Gene | Class | CR Prevention |
|---|---|---|---|---|---|---|---|
| U00445 | −4.3 | 1.4 | 39 | 132 | Glucose-6-phosphatase | Energy metabolism | 79 |
| W48504 | −4.1 | 1.1 | 32 | 78 | phosphoneuroprotein 14 homolog) | Unknown | N |
| AA153337 | −3.9 | 0.7 | 67 | 218 | Myosin regulatory light chain 2 (MLC-2) | Unknown | 61 |
| W51213 | −3.9 | 0.5 | 14 | 57 | NEDD-4 homolog | Protein metabolism | 55 |
| X56304 | −3.1 | 0.4 | 2 | 27 | Tenascin | Growth/development | N |
| W12681 | −3.1 | 0.6 | 30 | 126 | Hepatocyte growth factor | Growth/development | 37 |
| Z68889 | −2.9 | 1.0 | 30 | 70 | Wnt-2 homolog | Growth/development | N |
| W55684 | −2.8 | 0.6 | 13 | 37 | Brain protein i47 | Unknown | N |
| U04827 | −2.8 | 0.5 | 94 | 219 | Brain fatty acid-binding protein (B-FABP) | Growth/development | N |
| AA008066 | −2.7 | 1.0 | 1 | 61 | Pre-mRNA splicing factor PRP22 | Unknown | 74 |
| W55300 | −2.7 | 0.7 | 20 | 47 | Fatty acid-binding protein, heart (H-FABP) | Unknown | 71 |
| D13903 | −2.7 | 0.5 | 7 | 37 | MPTPdelta (type A) | Growth/development | N |
| AA013976 | −2.6 | 0.5 | 162 | 405 | POL polyprotein; reverse transcriptase ribonuclease H | Unknown | N |
| W10865 | −2.6 | 0.2 | 14 | 142 | Myosin light chair 1, atrial/foetal isoform | Unknown | N |
| AA020296 | −2.5 | 0.2 | −162 | 166 | NG9 | Growth/development | 100 |
| W64865 | −2.5 | 1.1 | 10 | 31 | Stat-3 | Unknown | N |
| AA139694 | −2.5 | 0.3 | 64 | 203 | Beta-myosin heavy chain | Transport | 100 |
| U29762 | −2.5 | 0.3 | 304 | 657 | Albumin gene D-Box binding protein | Transcription Factor | N |
| M87276 | −2.4 | 0.5 | 16 | 34 | Thrombospondin | Structural | 52 |
| X02677 | −2.4 | 0.2 | 63 | 160 | Anion exchange protein | Anion exchanger | 100 |
| X04836 | −2.4 | 0.2 | 22 | 68 | T-cell antigen CDA | Immune/inflammatory | 100 |
| X87242 | −2.4 | 0.3 | 48 | 111 | unc-33 | Growth/development | 70 |
| AA163021 | −2.4 | 0.2 | 28 | 43 | Annexin VIII | Signal transduction | 84 |
| M31810 | −2.4 | 0.3 | 29 | 113 | P-protein membrane transporter | Transport | 100 |
| M97900 | −2.4 | 0.6 | 18 | 49 | Unknown | Unknown | 20 |
| M15008 | −2.4 | 0.6 | 101 | 227 | Steroid 21-hydroxylase B | Steroid metabolism | 100 |
| M99377 | −2.4 | 0.5 | 77 | 191 | Alpha-2 adrenergic receptor | Neurotransmission | N |
| M32490 | −2.4 | 0.3 | 62 | 122 | Cyr61 | Growth/development | 41 |

TABLE 10-continued

Aging-related decreases in gene expression in the cerebellum of C57B/6 mice*

| ORF | Fold Change | SE | Signal Intensity Old | Young | Gene | Class | CR Prevention |
|---|---|---|---|---|---|---|---|
| AA168350 | −2.3 | 0.3 | 130 | 237 | Cysteinyl-tRNA synthetase | Protein metabolism | 83 |
| AA061206 | −2.3 | 0.2 | 8 | 52 | Unp (ubiquitin protease) | Protein metabolism | N |
| W12794 | −2.3 | 0.3 | 23 | 96 | Unknown | Unknown | 78 |
| AA050593 | −2.3 | 0.1 | 5 | 69 | Unknown | Unknown | 62 |
| AA050715 | −2.3 | 0.3 | 64 | 148 | Smoothelin | Structural | 92 |
| AA106463 | −2.2 | 0.3 | 110 | 277 | Phosphoenolpyruvate carboxykinase | Energy metabolism | N |
| X90829 | −2.2 | 0.3 | −16 | 9 | Lbx1 | Growth/development | N |
| X65588 | −2.2 | 0.3 | −1 | 24 | mp41 | Neurotransmission | N |
| J00475 | −2.2 | 0.2 | −23 | 58 | Ig alpha chain | Immune/inflammatory | N |
| X03019 | −2.2 | 0.3 | 4 | 71 | GM-CSF | Immune/inflammatory | 26 |
| W34687 | −2.2 | 0.4 | 62 | 115 | Alpha-actin | Transport | 78 |
| W75614 | −2.2 | 0.4 | 27 | 56 | Alpha-synuclein | Growth/development | N |
| AA068153 | −2.2 | 0.3 | 14 | 39 | Polyadenylate-binding protein | RNA metabolism | 55 |
| U36842 | −2.1 | 0.5 | 22 | 36 | Riap 3-inhibitor of apoptosis | Apoptosis | 100 |
| W09127 | −2.1 | 0.3 | 3 | 85 | 60S ribosomal protein L22 | Protein metabolism | 100 |
| D63819 | −2.1 | 0.2 | 29 | 87 | Neuropeptide Y-Y1 receptor | Neurotransmission | N |
| M33884 | −2.1 | 0.1 | 70 | 139 | Env polyprotein | Viral protein | 55 |
| AA144430 | −2.1 | 0.3 | 64 | 156 | NF-KB P100 inhibition subunit | Stress response | 48 |
| AA168554 | −2.1 | 0.3 | 119 | 246 | Unknown | Unknown | 85 |
| U35730 | −2.1 | 0.8 | 12 | 30 | Jerky | Unknown | N |
| M92649 | −2.1 | 0.4 | 45 | 112 | nitric oxide syntnase | Neurotransmission | N |
| D12907 | −2.1 | 0.2 | 55 | 126 | Serine protease inhibitor homologue | Unknown | 85 |
| M17327 | −2.1 | 0.2 | 234 | 566 | Env polyprotein | Viral protein | 56 |
| AA170444 | −2.1 | 0.2 | 172 | 246 | Ubiquitin-activating enzyme E1 | Protein metabolism | 100 |
| W12658 | −2.1 | 0.3 | 203 | 415 | FKBP-rapamycin associated protein | Unknown | N |
| AA123026 | −2.1 | 0.3 | 60 | 116 | REG 2 | Unknown | 100 |
| W13125 | −2.1 | 0.5 | 111 | 232 | Phenylalanyl-tRNA synthetase beta chain | Protein metabolism | N |
| AA103862 | −2.1 | 0.4 | 53 | 143 | Unknown | Unknown | N |
| U21301 | −2.1 | 0.6 | 30 | 62 | c-mer tyrosine kinase receptor | Signal transduction | N |
| W13586 | −2.1 | 0.1 | 29 | 136 | Myosin light chain 1 homolog | Transport | 100 |
| W42217 | −2.1 | 0.1 | 69 | 143 | Ribosonal protein S20 | Protein metabolism | 100 |
| AA153522 | −2.1 | 0.4 | 95 | 191 | Serine/threonine kinase | Signal transduction | 78 |
| W30612 | −2.0 | 0.1 | 70 | 160 | Chloride intracellular channel 3 | Transport | 100 |
| W11621 | −2.0 | 0.4 | 78 | 138 | Zinc finger protein 126 | Unknown | N |
| X72805 | −2.0 | 0.3 | 25 | 63 | CD-1 histone H1t | DNA metabolism | N |
| L08407 | −2.0 | 0.3 | 38 | 117 | Collagen type XVII | Structural | N |
| AA145609 | −2.0 | 0.2 | 55 | 134 | cAMP responsive element modifier | Transcripional factor | 34 |
| W12756 | −2.0 | 0.1 | 48 | 117 | Unknown | Unknown | 92 |
| W75523 | −2.0 | 0.3 | 48 | 95 | Vertebrate homolog of C. elegans Lin-7 type 2 | Unknown | N |
| D85904 | −1.9 | 0.3 | 69 | 129 | Heat shock 70-related protein Apg-2 | Stress response | N |
| AA138911 | −1.8 | 0.2 | 176 | 311 | RNA helicase PRP16 | RNA metabolism | 100 |
| W42216 | −1.8 | 0.1 | 183 | 361 | SWI/SNF related homolog | Transcriptional factor | 74 |
| W12395 | −1.8 | 0.4 | 141 | 237 | Transcription elongation factor A (SII) | Transcriptional factor | 88 |
| K03235 | −1.8 | 0.1 | 84 | 149 | Proliferin 2 | Growth factor | 100 |
| AA145859 | −1.8 | 0.1 | 4110 | 5250 | Unknown | Unknown | 100 |
| W57194 | −1.8 | 0.2 | 61 | 108 | Ubiquitin carboxyl terminal hydrolase 12 | Protein metabolism | N |
| AA166440 | −1.7 | 0.1 | 229 | 389 | Phosphatidylserine decarboxylase | Protein metabolism | N |
| L33726 | −1.7 | 0.1 | 69 | 128 | Fascin homolog 1 | Structural | 100 |
| L35549 | −1.7 | 0.4 | 30 | 38 | Y-box binding protein homolog | Unknown | 100 |
| AA154514 | −1.7 | 0.1 | 7639 | 12878 | ATP synthase A chain (protein 6) homolog | Energy metabolism | 100 |
| AA143937 | −1.7 | 0.1 | 384 | 697 | Beta-centractin | Transport | 70 |
| AA027387 | −1.7 | 0.1 | 169 | 270 | Rab-4B | Transport | 51 |
| L38971 | −1.7 | 0.2 | 205 | 334 | Integral membrane protein 2 | Unknown | 43 |
| W10526 | −1.7 | 0.1 | 193 | 301 | Ca− channel, voltage-dep., gamma subunit 1 | Transport | 90 |
| W12204 | −1.6 | 0.2 | 114 | 200 | Ca2+/calmodulin-dependent protein kinase isoform gamma B | Signal transduction | N |
| AA170173 | −1.6 | 0.1 | 149 | 289 | NTT-73 | Transport | 100 |
| M64403 | −1.6 | 0.1 | 126 | 208 | Cyclin D1 homolog | DNA metabolism | 100 |
| W13191 | −1.6 | 0.1 | 288 | 347 | Thyroid hormone receptor alpha 2 | Energy metabolism | 87 |
| U47543 | −1.6 | 0.1 | 121 | 205 | NGF1-A binding protein 2 (NAB2) | Growth factor | N |
| D70848 | −1.6 | 0.2 | 154 | 246 | Zic2 (cerebellar zinc finger protein) | Neural development | 77 |
| X56518 | −1.6 | 0.3 | 106 | 164 | Acetylcholinesterase | Neurotransmission | N |
| AA144588 | −1.6 | 0.2 | 233 | 368 | Beta-adrenergic receptor kinase 2 homolog | Neurotransmission | 33 |
| AA139828 | −1.6 | 0.1 | 224 | 351 | gonadotropin inducible transcription repressor-1 homolog | Unknown | 100 |
| AA061170 | −1.6 | 0.2 | 43 | 65 | WW-domain oxidoreductase homolog | Unknown | N |
| X58287 | −1.6 | 0.3 | 84 | 153 | mR-PTPu | Signal transduction | N |
| L13129 | −1.6 | 0.1 | 162 | 220 | Annexin A7 | Exocytosis | 90 |
| D85037 | −1.6 | 0.1 | 50 | 77 | Doc2beta | Neruotransmission | N |

TABLE 10-continued

Aging-related decreases in gene expression in the cerebellum of C57B/6 mice*

| ORF | Fold Change | SE | Signal Intensity Old | Young | Gene | Class | CR Prevention |
|---|---|---|---|---|---|---|---|
| U30823 | −1.6 | 0.2 | 55 | 102 | Myocyte enhancer factor-2A | Transciptional factor | 33 |
| W64791 | −1.6 | 0.1 | 92 | 143 | Galactokinese | Energy metabolism | N |
| X52622 | −1.6 | 0.1 | 274 | 377 | IN | Viral protein | 100 |
| AA063914 | −1.5 | 0.1 | 175 | 267 | Alpha-tubulin | Transport | 64 |

*The values presented for Signal Intensity are the averages of three mice per age group and are expressed as data for old/young mice. The prevention by CR is shown as being none (N) or the calculated percentage effect. The SE was calculated for the nine pairwise comparisons and was obtained by dividing the standard deviation by the square root of 3. The method from which siganl intensity is used to estimate fold changes is described in the Methods section of the manuscript.

TABLE 11

Genes upregulated by aging in C57BL/6 mice heart from Mu19K GeneChip

| Probe Set | oc1 | oc2 | oc3 | yc1 | yc2 | yc3 | Fold Change |
|---|---|---|---|---|---|---|---|
| TC27774 | 396 | 218 | 490 | −1328 | −2197 | −1280 | 25.8 |
| TC35932 | 71 | 1391 | 355 | −596 | −507 | −1500 | 17.2 |
| TC39719 | 938 | 595 | 1380 | 529 | −129 | −562 | 14.6 |
| TC24697 | 1510 | 2431 | 3697 | 173 | −823 | −537 | 13.9 |
| TC17809 | 4141 | 4286 | 4415 | 224 | 369 | 921 | 11.0 |
| TC28794 | 1358 | 1313 | 1445 | 349 | −38 | 657 | 10.4 |
| TC16257 | 439 | 867 | 471 | −121 | −528 | 166 | 10.3 |
| TC34515 | 1687 | 1117 | 966 | 465 | −1068 | −1737 | 9.4 |
| TC29214 | 102 | 154 | 188 | −381 | −122 | −209 | 9.0 |
| TC32857 | 733 | 915 | 524 | 200 | 82 | 90 | 8.3 |
| TC37114 | 553 | 803 | 466 | 377 | −99 | 59 | 8.2 |
| TC17940 | 947 | 1889 | 1474 | −54 | 160 | −1487 | 8.1 |
| TC39890 | 912 | 1658 | 1190 | 639 | 617 | 8 | 7.7 |
| TC39498 | 1080 | 738 | 1754 | −29 | 634 | −462 | 7.3 |
| TC25820 | 340 | 510 | 325 | −353 | −315 | −575 | 6.1 |
| TC24908 | 12482 | 8941 | 7330 | 1337 | 1838 | 1387 | 5.8 |
| TC29305 | 1271 | 1020 | 827 | 841 | 382 | 606 | 5.5 |
| TC16024 | 739 | 1570 | 995 | 603 | 312 | 123 | 4.8 |
| TC33899 | 304 | 287 | 240 | 64 | 30 | 73 | 4.8 |
| TC16184 | 1294 | 3064 | 3523 | 428 | 388 | 447 | 4.7 |
| TC39399 | 338 | 421 | 286 | −81 | 208 | 27 | 4.5 |
| TC17839 | 1506 | 946 | 2315 | 248 | 512 | 146 | 4.5 |
| TC18386 | 1822 | 1967 | 1585 | 281 | 566 | 477 | 4.4 |
| TC27769 | 3796 | 5647 | 3986 | 1260 | 975 | 2286 | 4.4 |
| TC37583 | 433 | 617 | 758 | 119 | 425 | 93 | 4.3 |
| TC22269 | 6795 | 7593 | 8793 | 920 | 2322 | 5205 | 4.1 |
| TC28239 | 2039 | 1359 | 881 | 227 | 495 | 604 | 4.1 |
| TC34440 | 340 | 310 | 258 | 21 | −437 | −170 | 4.1 |
| TC39301 | 803 | 1692 | 1539 | 27 | 710 | 778 | 4.1 |
| TC29662 | 997 | 2372 | 1701 | 174 | 650 | 694 | 4.0 |
| TC33757 | 339 | 323 | 257 | 49 | 76 | 231 | 3.9 |
| TC29977 | 858 | 631 | 879 | 102 | 541 | 335 | 3.9 |
| TC19997 | 419 | 358 | 384 | 84 | 67 | 266 | 3.8 |
| TC27675 | 4002 | 5625 | 6693 | 1292 | 1580 | 1426 | 3.8 |
| TC21921 | 677 | 779 | 864 | 339 | 43 | 229 | 3.8 |
| TC41800 | 915 | 441 | 1157 | −8 | 69 | 180 | 3.7 |
| TC31694 | 2158 | 2467 | 2245 | 449 | 306 | 976 | 3.7 |
| TC28855 | 282 | 194 | 355 | 67 | 127 | 62 | 3.6 |
| TC31277 | 311 | 243 | 445 | 44 | 182 | 172 | 3.6 |
| TC21628 | 176 | 422 | 304 | 124 | 76 | 68 | 3.5 |
| TC36063 | 498 | 623 | 390 | −80 | 346 | −52 | 3.5 |
| TC33608 | 514 | 449 | 479 | 140 | 165 | 124 | 3.4 |
| TC38147 | 420 | 212 | 473 | 61 | 173 | 211 | 3.3 |
| TC23622 | 112 | 328 | 186 | −55 | 60 | 99 | 3.2 |
| TC34697 | 549 | 450 | 752 | 89 | 356 | 370 | 3.2 |
| TC22213 | 1892 | 2305 | 2099 | 655 | 730 | 644 | 3.1 |
| TC31569 | 282 | 113 | 247 | 73 | 127 | 4 | 3.1 |
| TC28942 | 517 | 1055 | 1020 | 301 | 364 | 224 | 3.0 |

TABLE 12

Genes downregulated by aging in C57BL/6 mice heart from Mu19K GeneChip

| Probe Set | oc1 | oc2 | oc3 | yc1 | yc2 | yc3 | Fold Change |
|---|---|---|---|---|---|---|---|
| TC27282 | 20 | −2020 | −2141 | 5078 | 970 | 879 | −86.2 |
| TC32064 | −217 | −844 | −511 | 2335 | 2211 | 2176 | −58.6 |
| TC24160 | 1155 | −3091 | −2382 | 427 | 4103 | 4674 | −56.2 |
| TC14603 | 867 | −2795 | −2128 | 4729 | 2680 | 2255 | −53.4 |
| TC22507 | −1155 | −1599 | −1409 | 1319 | 2177 | 2942 | −50.4 |
| TC15929 | −1203 | −1586 | −1787 | 1348 | 1014 | 2026 | −47.0 |
| TC19943 | −687 | −669 | −428 | 2880 | 2552 | 1067 | −41.7 |
| TC18736 | −1142 | 787 | −1647 | 2711 | 3654 | 4006 | −33.0 |
| TC19957 | 1242 | −501 | 958 | 6796 | 6771 | 5343 | −30.5 |
| TC37452 | 175 | −1172 | −441 | 820 | 2013 | 1233 | −27.3 |
| TC33452 | 532 | −740 | −465 | 2021 | 880 | 719 | −26.3 |
| TC14870 | −289 | −1650 | −2496 | 30 | 209 | 1249 | −25.2 |
| TC26312 | −118 | −73 | −146 | 406 | 1251 | 1344 | −24.3 |
| TC25802 | −688 | −736 | −1968 | 31 | 707 | 695 | −23.7 |
| TC14624 | −227 | −943 | −758 | 1675 | 718 | 352 | −22.6 |
| TC41568 | −684 | −3089 | −1954 | 7 | 711 | 129 | −22.6 |
| TC46488 | −1548 | −57 | −1609 | 1055 | 1739 | 190 | −22.5 |
| TC18539 | 122 | 1114 | −269 | 3415 | 2604 | 2614 | −21.6 |
| TC37617 | 1738 | −296 | −2150 | 2156 | 2231 | 422 | −20.6 |
| TC39618 | 56 | −204 | −168 | 769 | 1196 | 887 | −19.5 |
| TC37350 | 1070 | −657 | −655 | 1944 | 1258 | 260 | −19.5 |
| TC36639 | 1496 | −3251 | −23 | 4489 | 2756 | 6211 | −19.4 |
| TC16420 | 48 | −674 | −17 | 1059 | 1053 | 1072 | −18.6 |
| TC37529 | 177 | 151 | 333 | 6190 | 3159 | 2499 | −18.3 |
| TC15736 | 67 | −1109 | −1133 | 242 | 530 | 647 | −18.2 |
| TC36992 | 498 | −2096 | −450 | 2140 | 2451 | 1214 | −17.9 |
| TC28761 | 326 | −105 | 847 | 4047 | 2990 | 1712 | −17.9 |
| TC25360 | −1421 | −2210 | −2177 | 332 | 173 | 204 | −17.2 |
| TC16633 | −66 | −612 | −638 | 626 | 240 | 496 | −17.0 |
| TC18250 | 145 | −416 | −464 | 2429 | 890 | 804 | −16.3 |
| TC35586 | −337 | −526 | 6 | 762 | 782 | 328 | −16.2 |
| TC37067 | 2006 | 137 | 2589 | 7334 | 6130 | 5348 | −16.0 |
| TC40509 | 176 | −216 | 197 | 2219 | 724 | 1177 | −15.9 |
| TC37745 | 380 | −1137 | 141 | 822 | 1566 | 1043 | −15.8 |
| TC24220 | 648 | 227 | 48 | 1916 | 1805 | 2138 | −14.9 |
| TC17700 | 159 | −80 | −657 | 565 | 810 | 690 | −14.4 |
| TC17256 | 2800 | −3715 | −3550 | 629 | 2754 | 950 | −13.4 |
| TC37672 | 117 | 427 | 247 | 1149 | 1712 | 1737 | −13.0 |
| TC18637 | 202 | −208 | −312 | 1012 | 907 | 794 | −12.8 |
| TC15863 | −639 | 250 | 289 | 882 | 794 | 1198 | −12.7 |
| TC23647 | −575 | 334 | −1428 | 1821 | 2149 | 2101 | −12.5 |
| TC16841 | 375 | −198 | 430 | 1177 | 1044 | 1257 | −12.3 |
| TC27576 | −70 | 75 | 428 | 596 | 1326 | 857 | −12.2 |
| TC21963 | −281 | −437 | −368 | 944 | 136 | 231 | −12.2 |
| TC36608 | −527 | −316 | −140 | 343 | 254 | 7 | −12.1 |
| TC26887 | 60 | 188 | −100 | 589 | 933 | 734 | −11.9 |
| TC24501 | 539 | 518 | 79 | 4279 | 1947 | 1811 | −11.8 |
| TC36239 | 902 | −102 | 843 | 1587 | 1899 | 2152 | −11.3 |
| TC38050 | 47 | −81 | 115 | 324 | 633 | 645 | −11.3 |
| TC37660 | −1 | −617 | −203 | 450 | 240 | 314 | −11.1 |
| TC34986 | −1 | −98 | −28 | 726 | 315 | 235 | −10.7 |

TABLE 12-continued

Genes downregulated by aging in C57BL/6 mice heart from Mu19K GeneChip

| Probe Set | oc1 | oc2 | oc3 | yc1 | yc2 | yc3 | Fold Change |
|---|---|---|---|---|---|---|---|
| TC30885 | 402 | −55 | 27 | 878 | 734 | 398 | −10.4 |
| TC16723 | 478 | 276 | 62 | 1703 | 1736 | 1138 | −10.3 |
| TC20671 | −70 | −827 | −303 | 948 | 1087 | 410 | −10.2 |
| TC14753 | −332 | −265 | −325 | 418 | 335 | 276 | −10.1 |
| TC16229 | −156 | 515 | 107 | 1224 | 681 | 1077 | −10.1 |
| TC24641 | −372 | −382 | −329 | 127 | 845 | 718 | −10.0 |
| TC35052 | 139 | −86 | −19 | 504 | 459 | 447 | −9.9 |
| TC20554 | 158 | 392 | 625 | 1255 | 896 | 1199 | −9.8 |
| TC25572 | 470 | −460 | −871 | 472 | 1340 | 791 | −9.5 |
| TC21262 | 220 | −336 | 1193 | 2061 | 1581 | 2928 | −9.5 |
| TC25416 | 48 | −285 | −104 | 487 | 554 | 460 | −9.5 |
| TC41297 | 373 | −176 | 455 | 1093 | 976 | 991 | −9.4 |
| TC37701 | −219 | −338 | −398 | 830 | 294 | 236 | −9.4 |
| TC34944 | 364 | 462 | 369 | 3507 | 3271 | 3393 | −9.3 |
| TC31449 | −7 | 53 | −51 | 300 | 252 | 217 | −9.0 |
| TC41997 | 167 | −142 | 199 | 682 | 1057 | 893 | −8.8 |
| TC36933 | −164 | −295 | −678 | 1048 | 194 | 241 | −8.8 |
| TC27468 | 584 | 492 | 560 | 1011 | 1031 | 929 | −8.8 |
| TC16039 | 603 | −2181 | −1612 | 2105 | 1544 | 1004 | −8.6 |
| TC19352 | 918 | −290 | −600 | 1103 | 700 | 859 | −8.5 |
| TC25041 | 229 | −697 | −295 | 726 | 515 | 558 | −8.4 |
| TC35104 | 548 | 1 | 563 | 1294 | 1692 | 715 | −8.3 |
| TC25357 | 143 | −277 | −40 | 897 | 788 | 1407 | −8.0 |
| TC22194 | 119 | −63 | −176 | 477 | 440 | 633 | −7.9 |
| TC20469 | 284 | −303 | −850 | 1031 | 591 | 674 | −7.7 |
| TC41078 | −35 | −289 | 42 | 551 | 222 | 148 | −7.7 |
| TC39603 | 417 | −253 | 300 | 813 | 952 | 586 | −7.6 |
| TC36846 | 64 | −83 | 117 | 606 | 487 | 353 | −7.2 |
| TC24619 | −11 | −273 | −224 | 212 | 483 | 418 | −7.1 |
| TC15831 | 1167 | 1269 | 87 | 3253 | 1942 | 1814 | −7.1 |
| TC25629 | −4 | −309 | −341 | 387 | 106 | 167 | −7.1 |
| TC23144 | −91 | −175 | −322 | 770 | 114 | 393 | −7.0 |
| TC29553 | 77 | −27 | −110 | 93 | 283 | 185 | −7.0 |
| TC36286 | −312 | −574 | −44 | 702 | 929 | 668 | −6.8 |
| TC23964 | 1265 | 1225 | 276 | 6611 | 4409 | 5007 | −6.8 |
| TC37675 | 19 | 103 | 139 | 408 | 734 | 469 | −6.6 |
| TC41144 | 236 | 58 | 273 | 1095 | 734 | 708 | −6.6 |
| TC40883 | −31 | −251 | 88 | 201 | 473 | 370 | −6.6 |
| TC27606 | −640 | −765 | −579 | 232 | 208 | 394 | −6.5 |
| TC14712 | 1140 | 643 | −15 | 1661 | 1331 | 2644 | −6.5 |
| TC26859 | 803 | 95 | 985 | 3249 | 2325 | 2184 | −6.4 |
| TC33246 | 168 | −216 | −384 | 517 | 283 | 384 | −6.4 |
| TC37343 | 180 | −27 | 34 | 459 | 508 | 346 | −6.3 |
| TC37275 | 1193 | 720 | 808 | 1722 | 1828 | 1992 | −6.3 |
| TC18134 | 685 | 695 | 488 | 145 | 57 | 96 | −6.2 |
| TC40210 | 166 | −245 | 91 | 354 | 502 | 400 | −6.1 |
| TC17241 | 438 | −110 | 756 | 1750 | 2691 | 2519 | −6.1 |
| TC21038 | 133 | −138 | −206 | 600 | 218 | 168 | −6.1 |
| TC22355 | 12 | −396 | −116 | 182 | 232 | 177 | −6.1 |
| TC38075 | 111 | −40 | 11 | 533 | 588 | 613 | −6.0 |
| TC38184 | −263 | −107 | 58 | 293 | 235 | 92 | −6.0 |
| TC37491 | 239 | 166 | 349 | 1404 | 1500 | 1141 | −5.9 |
| TC33420 | −132 | −208 | −114 | 388 | 128 | 88 | −5.9 |
| TC37318 | 1331 | 188 | 833 | 1241 | 3321 | 2861 | −5.8 |
| TC37916 | −273 | −62 | −202 | 198 | 55 | 43 | −5.8 |
| TC17885 | −178 | 169 | −288 | 1591 | 1472 | 1445 | −5.7 |
| TC15884 | 390 | −134 | −109 | 734 | 431 | 493 | −5.6 |
| TC40452 | −94 | −141 | 107 | 291 | 339 | 359 | −5.6 |
| TC29330 | 512 | 370 | 140 | 2164 | 1174 | 930 | −5.6 |
| TC17616 | 101 | 46 | 57 | 531 | 853 | 808 | −5.6 |
| TC21414 | −62 | −2 | −143 | 111 | 296 | 344 | −5.5 |
| TC17717 | 36 | −83 | −144 | 222 | 172 | 209 | −5.4 |
| TC31495 | 156 | 155 | 77 | 280 | 502 | 371 | −5.3 |
| TC18144 | 2048 | 819 | 1400 | 3236 | 3117 | 3190 | −5.3 |
| TC19650 | −120 | −282 | −56 | 358 | 86 | 18 | −5.2 |
| TC25815 | 36 | 224 | 90 | 490 | 506 | 508 | −5.2 |
| TC37544 | 470 | 242 | 458 | 527 | 767 | 691 | −5.1 |
| TC38870 | 119 | −35 | 187 | 1057 | 704 | 587 | −5.1 |
| TC26789 | 111 | 49 | −68 | 240 | 243 | 270 | −5.0 |
| TC37493 | 103 | 250 | 396 | 993 | 982 | 795 | −5.0 |
| TC41579 | 465 | 120 | 253 | 959 | 557 | 669 | −5.0 |
| TC17620 | 326 | 452 | 303 | 721 | 565 | 788 | −4.9 |
| TC18572 | 29 | −130 | −51 | 208 | 264 | 348 | −4.9 |
| TC41021 | 217 | 84 | 43 | 611 | 329 | 306 | −4.9 |
| TC25021 | 61 | 95 | 69 | 471 | 440 | 235 | −4.9 |
| TC37829 | −235 | −243 | 92 | 142 | 292 | 771 | −4.7 |
| TC19783 | 35 | −10 | 249 | 371 | 604 | 767 | −4.6 |
| TC24373 | −111 | −424 | 171 | 376 | 384 | 395 | −4.6 |
| TC41191 | 54 | −407 | −30 | 741 | 36 | 721 | −4.6 |
| TC30942 | 281 | 146 | 19 | 1772 | 1068 | 1025 | −4.5 |
| TC14554 | 28 | −147 | 44 | 651 | 479 | 471 | −4.5 |
| TC32618 | 210 | 68 | 260 | 435 | 504 | 448 | −4.5 |
| TC35574 | 1063 | 295 | 1619 | 2598 | 3642 | 3046 | −4.5 |
| TC39584 | 1090 | 1014 | 538 | 2430 | 3908 | 4185 | −4.4 |
| TC37290 | −26 | −15 | 90 | 541 | 212 | 211 | −4.3 |
| TC14567 | 968 | 216 | 267 | 2605 | 1842 | 1044 | −4.2 |
| TC30986 | 66 | −14 | 76 | 306 | 151 | 178 | −4.2 |
| TC35356 | 211 | −3 | 224 | 474 | 598 | 338 | −4.2 |
| TC35554 | 91 | −100 | 89 | 572 | 566 | 558 | −4.2 |
| TC22851 | 810 | 416 | 520 | 3098 | 1773 | 1661 | −4.2 |
| TC20860 | 316 | 118 | 498 | 1291 | 739 | 695 | −4.1 |
| TC41573 | 212 | 88 | 343 | 656 | 1162 | 931 | −4.1 |
| TC32333 | 471 | 489 | 542 | 2274 | 1696 | 1350 | −4.1 |
| TC20845 | 164 | 222 | −12 | 508 | 438 | 361 | −4.0 |
| TC37484 | 192 | −14 | 236 | 408 | 384 | 494 | −4.0 |
| TC33993 | −342 | −140 | −253 | 161 | 567 | 752 | −4.0 |
| TC37769 | 670 | 107 | 485 | 2676 | 1219 | 1617 | −3.9 |
| TC31667 | 435 | 73 | 167 | 1141 | 556 | 585 | −3.9 |
| TC18679 | 1123 | 1055 | 1090 | 638 | 626 | 366 | −3.9 |
| TC21666 | 5 | 81 | −153 | 203 | 351 | 195 | −3.8 |
| TC41350 | 213 | 83 | 206 | 680 | 403 | 479 | −3.8 |
| TC21304 | −109 | −65 | −63 | 243 | 38 | 61 | −3.7 |
| TC39507 | −137 | −208 | −77 | 310 | 61 | 22 | −3.7 |
| TC19129 | 827 | 722 | 469 | 1364 | 1364 | 1142 | −3.6 |
| TC21197 | −376 | −1186 | −1054 | 1746 | 1222 | 416 | −3.6 |
| TC38888 | 67 | 8 | 50 | 292 | 106 | 199 | −3.6 |
| TC32452 | 992 | 974 | 1165 | 2411 | 2887 | 2965 | −3.5 |
| TC14511 | 739 | 660 | 298 | 942 | 1924 | 2211 | −3.5 |
| TC29246 | 716 | 546 | 538 | 1125 | 991 | 1222 | −3.4 |
| TC15902 | 137 | −4 | 55 | 350 | 211 | 209 | −3.4 |
| TC37774 | 378 | 234 | 424 | 1148 | 1146 | 952 | −3.3 |
| TC27288 | 377 | 394 | 816 | 1451 | 1663 | 1554 | −3.3 |
| TC31668 | −76 | −153 | −46 | 170 | 103 | 10 | −3.3 |
| TC41983 | 252 | −1 | 190 | 240 | 490 | 429 | −3.3 |
| TC14823 | 933 | 420 | 557 | 1168 | 2494 | 1983 | −3.3 |
| TC40714 | 416 | 939 | 354 | 1914 | 1744 | 1041 | −3.3 |
| TC20259 | 272 | 22 | 86 | 330 | 285 | 513 | −3.3 |
| TC23344 | 462 | 577 | 862 | 1602 | 2043 | 2131 | −3.3 |
| TC27282 | 1068 | 765 | 508 | 3300 | 1911 | 1689 | −3.2 |
| TC21501 | 500 | 1332 | 782 | 4505 | 3307 | 3468 | −3.2 |
| TC34693 | −14 | 177 | 761 | 1242 | 1088 | 1137 | −3.2 |
| TC41186 | 231 | 120 | 272 | 1122 | 579 | 641 | −3.1 |
| TC26149 | 276 | −43 | 141 | 279 | 541 | 452 | −3.1 |
| TC20981 | −59 | −53 | −38 | 137 | 67 | 86 | −3.1 |
| TC39851 | 97 | −176 | 80 | 457 | 204 | 169 | −3.0 |
| TC26095 | 283 | 532 | 336 | 1142 | 776 | 909 | −3.0 |
| TC16932 | 125 | 188 | 91 | 490 | 284 | 323 | −3.0 |
| TC22052 | 100 | 118 | 149 | 375 | 356 | 323 | −3.0 |

TABLE 13

Genes upregulated by aging in C57BL/6 mice heart from Mu6500 GeneChip

| ORF | oc1 | oc2 | oc3 | yc1 | yc2 | yc3 | Fold Change |
|---|---|---|---|---|---|---|---|
| X60103 | 242 | 223 | 238 | 13 | −52 | 65 | 11.8 |
| M117446 | 273 | 512 | 453 | 155 | 118 | 66 | 6.8 |
| M21829 | 82 | 83 | 141 | 24 | 45 | 52 | 5.4 |
| L07297 | 69 | 103 | 101 | −52 | −30 | −43 | 5.1 |

TABLE 13-continued

Genes upregulated by aging in C57BL/6 mice heart from Mu6500 GeneChip

| ORF | oc1 | oc2 | oc3 | yc1 | yc2 | yc3 | Fold Change |
|---|---|---|---|---|---|---|---|
| X94998 | 208 | 168 | 223 | −8 | −35 | 80 | 5.1 |
| W36875 | 149 | 126 | 153 | 15 | 64 | 64 | 4.9 |
| U00677 | 171 | 108 | 187 | 18 | 77 | 5 | 4.3 |
| M17440 | 311 | 354 | 372 | 90 | 84 | 61 | 4.0 |
| U08210 | 45 | 24 | 38 | −10 | 4 | −17 | 3.9 |
| AA097087 | 326 | 628 | 684 | 140 | 181 | 143 | 3.5 |
| X62622 | 180 | 134 | 235 | 81 | 112 | 27 | 3.5 |
| U25844 | 702 | 607 | 584 | 186 | 204 | 191 | 3.3 |
| D13664 | 218 | 202 | 130 | 40 | 75 | 75 | 3.3 |
| U00674 | 55 | 48 | 15 | −9 | 11 | 15 | 3.3 |
| Z31663 | 0 | 63 | 55 | −42 | −100 | −88 | 3.2 |
| X91824 | 155 | 121 | 140 | 58 | 60 | 69 | 3.2 |
| M152695 | 38 | 42 | 26 | 8 | 8 | 14 | 3.2 |
| M014024 | 111 | 219 | 218 | 110 | 59 | 72 | 3.1 |
| D16497 | 1888 | 1428 | 3023 | 664 | 996 | 517 | 3.1 |
| AA036050 | 52 | 52 | 49 | 18 | 9 | 9 | 3.1 |
| L41154 | 408 | 305 | 476 | 128 | 152 | 157 | 3.1 |
| L20276 | 1761 | 1059 | 1201 | 260 | 600 | 829 | 3.0 |
| M168633 | 585 | 654 | 733 | 167 | 253 | 246 | 3.1 |

TABLE 14

Genes downregulated by aging in C57BL/6 mice heart from Mu6500 GeneChip

| ORF | oc4 | oc5 | oc6 | yc1 | yc2 | yc3 | Fold Change |
|---|---|---|---|---|---|---|---|
| X54149 | 52 | 16 | −69 | 106 | 139 | 84 | −6.2 |
| X98475 | −7 | 37 | 38 | 202 | 136 | 79 | −6.1 |
| U25114 | 185 | 133 | 69 | 326 | 301 | 283 | −5.4 |
| U58885 | −16 | 33 | 105 | 315 | 212 | 301 | −5.3 |
| X85169 | −1 | −32 | −75 | 48 | 43 | 11 | −5.0 |
| M028728 | 68 | −19 | 17 | 90 | 99 | 116 | −4.9 |
| D14336 | 100 | 17 | 26 | 141 | 202 | 176 | −4.8 |
| W29790 | 72 | 91 | 13 | 259 | 196 | 195 | −4.8 |
| L11163 | 181 | 334 | −18 | 401 | 820 | 512 | −4.5 |
| AA068712 | 18 | −12 | −15 | 61 | 69 | 70 | −4.5 |
| D43643 | 26 | −12 | −58 | 69 | 61 | 45 | −4.3 |
| Y08361 | 35 | 1 | −35 | 88 | 54 | 84 | −4.2 |
| W57425 | −6 | −31 | −61 | 36 | 9 | 13 | −4.2 |
| L17076 | 130 | 103 | 97 | 645 | 491 | 431 | −4.1 |
| U08215 | 45 | 27 | −1 | 160 | 74 | 73 | −3.8 |
| M068780 | 28 | −5 | −34 | 86 | 32 | 64 | −3.8 |
| M072334 | 66 | 43 | 88 | 194 | 160 | 136 | −3.7 |
| M060808 | 98 | 30 | 57 | 226 | 159 | 155 | −3.7 |
| W84060 | 15 | 36 | 6 | 56 | 91 | 63 | −3.7 |
| X97796 | 16 | 5 | −24 | 72 | 53 | 37 | −3.6 |
| X60831 | 49 | 35 | 7 | 52 | 59 | 84 | −3.6 |
| M003162 | 152 | 28 | 108 | 274 | 204 | 224 | −3.6 |
| W08293 | 174 | 130 | 106 | 508 | 356 | 342 | −3.5 |
| M107999 | 47 | 6 | −18 | 77 | 72 | 56 | −3.5 |
| Z47205 | 112 | 93 | 21 | 127 | 181 | 253 | −3.3 |
| M107137 | 46 | −19 | −31 | 87 | 165 | 125 | −3.2 |
| U70017 | 34 | 0 | 3 | 126 | 63 | 48 | −3.2 |
| W34891 | 0 | 19 | 19 | 41 | 40 | 36 | −3.2 |
| M90364 | 141 | 94 | 103 | 394 | 273 | 326 | −3.1 |
| W20652 | 26 | 43 | 38 | 75 | 63 | 84 | −3.1 |
| W10926 | 48 | −1 | −5 | 99 | 34 | 82 | −3.1 |
| X53532 | 13 | 14 | 15 | 92 | 36 | 57 | −3.0 |
| W77701 | 167 | 90 | 68 | 369 | 347 | 251 | −3.0 |
| U53455 | 22 | 29 | 24 | 127 | 62 | 85 | −3.0 |
| U09218 | 17 | 22 | 2 | 57 | 71 | 29 | −3.0 |
| D78141 | 29 | 24 | 5 | 54 | 74 | 65 | −3.0 |

TABLE 15

Genes upregulated by aging in C57BL/6 mice gastrocnemius from Mu19K GeneChip

| Probe Set | oc1 | oc2 | oc3 | yc1 | yc2 | yc3 | Fold Change |
|---|---|---|---|---|---|---|---|
| TC22507 | 1496 | 5100 | 4680 | −861 | −868 | 2232 | 12.3 |
| TC41260 | 2271 | 2776 | 1202 | 345 | 337 | 214 | 7.1 |
| TC15427 | 3952 | 6832 | 4863 | 392 | 2541 | 1658 | 6.2 |
| TC17528 | 309 | 830 | 202 | −401 | −87 | 58 | 4.8 |
| TC39719 | 467 | 1194 | 956 | −96 | −68 | 639 | 4.6 |
| TC30023 | 3484 | 1557 | 2722 | −471 | 784 | −100 | 4.2 |
| TC15105 | 2869 | 2887 | 744 | 424 | 221 | −401 | 4.2 |
| TC22814 | 9874 | 12120 | 6784 | 1463 | 3030 | 4227 | 4.2 |
| TC32898 | 3770 | 1780 | 2282 | 1470 | 299 | 598 | 4.0 |
| TC17624 | 932 | 1910 | 1154 | 96 | 704 | 295 | 3.9 |
| TC38243 | 3651 | 2564 | 2668 | 2227 | 1427 | 370 | 3.3 |
| TC32537 | 2652 | 2455 | 3025 | 723 | 614 | 1165 | 3.3 |
| TC16833 | 1263 | 1056 | 635 | 427 | 417 | −26 | 3.1 |
| TC37853 | 655 | 965 | 895 | 237 | 151 | 275 | 3.1 |
| TC35747 | 768 | 1198 | 1174 | 477 | 809 | 145 | 3.0 |
| TC36248 | 3727 | 6677 | 4613 | 2357 | 2860 | 1045 | 2.9 |
| TC16809 | 2167 | 1306 | 1781 | 648 | 1219 | 566 | 2.8 |
| TC37410 | 1198 | 1044 | 612 | 564 | 545 | 38 | 2.8 |
| TC29110 | 1462 | 775 | 696 | −808 | −441 | −1038 | 2.7 |
| TC41340 | 615 | 744 | 603 | 435 | 182 | 403 | 2.7 |
| TC20762 | 1280 | 839 | 1046 | 582 | 553 | 149 | 2.7 |
| TC41486 | 2628 | 3390 | 2900 | 754 | 2234 | 1251 | 2.7 |
| TC30327 | 3780 | 2597 | 2167 | 628 | 1606 | 1354 | 2.6 |
| TC41030 | 402 | 383 | 450 | 125 | −70 | −187 | 2.6 |
| TC37927 | 1283 | 1988 | 419 | −684 | −704 | −690 | 2.5 |
| TC35232 | 206 | 291 | 846 | −414 | −154 | −217 | 2.5 |
| TC40552 | 676 | 624 | 566 | 180 | 272 | −14 | 2.5 |
| TC35879 | 761 | 606 | 643 | 217 | 248 | 316 | 2.5 |

TABLE 15-continued

Genes upregulated by aging in C57BL/6 mice gastrocnemius from Mu19K GeneChip

| Probe Set | oc1 | oc2 | oc3 | yc1 | yc2 | yc3 | Fold Change |
|---|---|---|---|---|---|---|---|
| TC36106 | 553 | 81 | 381 | 35 | −28 | −309 | 2.4 |
| TC14958 | 431 | 569 | 687 | 37 | 86 | 338 | 2.4 |
| TC15563 | 1782 | 2034 | 1615 | 779 | 1031 | 423 | 2.4 |
| TC37009 | 5627 | 4674 | 6716 | 3156 | 3535 | 2177 | 2.4 |
| TC38613 | 14275 | 16183 | 14699 | 6963 | 8380 | 4717 | 2.4 |
| TC17122 | 5461 | 6072 | 4547 | 2524 | 2633 | 1687 | 2.4 |
| TC27769 | 44054 | 58886 | 54326 | 31194 | 27436 | 14076 | 2.4 |
| TC33822 | 6543 | 3341 | 4435 | 1353 | 2737 | 2536 | 2.4 |
| TC20391 | 102 | 324 | 227 | −201 | −286 | −15 | 2.4 |
| TC38653 | 687 | 826 | 298 | 244 | 59 | 122 | 2.4 |
| TC40473 | 533 | 539 | 263 | 57 | 118 | 124 | 2.3 |
| TC17622 | 1714 | 1541 | 1071 | 926 | 397 | 609 | 2.3 |
| TC18112 | 756 | 793 | 703 | 610 | 211 | 251 | 2.3 |
| TC19062 | 2563 | 4000 | 2391 | 1565 | 2019 | 1229 | 2.3 |
| TC16585 | 4312 | 3985 | 4720 | 2520 | 2316 | 1346 | 2.3 |
| TC37317 | 726 | 1068 | 673 | 494 | 398 | 258 | 2.3 |
| TC40165 | 817 | 869 | 775 | 448 | 588 | 182 | 2.2 |
| TC21714 | 1174 | 1390 | 1120 | 808 | 475 | 702 | 2.2 |
| TC17422 | 31965 | 35070 | 40903 | 13173 | 19477 | 14605 | 2.2 |
| TC37018 | 592 | 437 | 367 | 217 | 172 | 79 | 2.2 |
| TC16885 | 2486 | 2538 | 923 | −830 | 765 | −522 | 2.2 |
| TC34291 | 13707 | 19389 | 10341 | 8383 | 5255 | 6689 | 2.2 |
| TC37463 | 1444 | 1417 | 1078 | 922 | 520 | 513 | 2.2 |
| TC24549 | 8515 | 9554 | 5391 | 4618 | 4038 | 3446 | 2.2 |
| TC35324 | 321 | 607 | 357 | 140 | 137 | 156 | 2.1 |
| TC31058 | 1436 | 1266 | 1773 | 514 | 303 | 159 | 2.1 |
| TC15920 | 2072 | 2001 | 1360 | 477 | 1197 | 809 | 2.1 |
| TC29793 | 1532 | 1993 | 2224 | 458 | 1173 | 801 | 2.1 |
| TC37926 | 2769 | 2562 | 1750 | 865 | 1108 | 1169 | 2.1 |
| TC40454 | 1344 | 2480 | 2437 | 590 | 1123 | 786 | 2.1 |
| TC17515 | 3386 | 4354 | 3900 | 2340 | 2892 | 1179 | 2.1 |
| TC35819 | 2072 | 2558 | 2188 | 1248 | 1174 | 959 | 2.1 |
| TC39079 | 1639 | 1879 | 1394 | 538 | 1352 | 726 | 2.1 |
| TC35125 | 1031 | 714 | 880 | 300 | 652 | 40 | 2.0 |
| TC40951 | 11 | 565 | 108 | −204 | −192 | −530 | 2.0 |
| TC37262 | 680 | 922 | 706 | 269 | 530 | 3 | 2.0 |
| TC31287 | 2040 | 2088 | 2058 | 336 | 1232 | 1246 | 2.0 |
| TC40137 | 334 | 303 | 464 | 69 | 135 | 144 | 2.0 |
| TC31251 | 1652 | 1328 | 1412 | 654 | 696 | 592 | 2.0 |
| TC31522 | 6212 | 5990 | 6621 | 3005 | 3336 | 4224 | 2.0 |
| TC37833 | 1464 | 1782 | 872 | 587 | 766 | 423 | 2.0 |
| TC23026 | 462 | 265 | 318 | 105 | 88 | 74 | 2.0 |
| TC33710 | 5381 | 4005 | 5984 | 1782 | 3214 | 2638 | 2.0 |
| TC14237 | 978 | 1638 | 1423 | 877 | 412 | 747 | 2.0 |
| TC32046 | 2438 | 2103 | 1415 | 898 | 512 | 1318 | 2.0 |
| TC15245 | 2305 | 2606 | 4096 | 1771 | 1589 | 503 | 2.0 |
| TC30375 | 15067 | 24645 | 27999 | 11194 | 14149 | 9870 | 2.0 |
| TC24289 | 383 | 454 | 679 | 143 | 283 | −134 | 2.0 |
| TC30683 | 1269 | 622 | 565 | −320 | 97 | 122 | 2.0 |

TABLE 16

Genes downregulated by aging in C57BL/6 mice gastrocnemius from Mu19K GeneChip

| Probe Set | oc1 | oc2 | oc3 | yc1 | yc2 | yc3 | Fold Change |
|---|---|---|---|---|---|---|---|
| TC39172 | 282 | 384 | 1189 | 1388 | 1492 | 1767 | −8.6 |
| TC24050 | −1117 | −243 | 252 | 388 | 1315 | 2392 | −6.8 |
| TC34953 | 3835 | 5266 | 6073 | 35656 | 21430 | 31766 | −6.3 |
| TC34306 | 1324 | 565 | −353 | 1427 | 2241 | 3278 | −5.6 |
| TC26537 | 3726 | 2008 | 378 | 6454 | 4146 | 9861 | −5.2 |
| TC35355 | 245 | 492 | 187 | 765 | 951 | 1217 | −4.9 |
| TC40742 | −394 | 229 | 395 | 1281 | 1132 | 1041 | −4.7 |
| TC24501 | 152 | 253 | −108 | 981 | 536 | 1084 | −4.6 |
| TC14421 | 419 | 1398 | 344 | 2366 | 1833 | 2615 | −4.5 |
| TC21687 | −959 | 88 | 1433 | 2686 | 2066 | 2732 | −4.5 |
| TC25229 | 369 | −201 | 79 | 1383 | 638 | 1283 | −4.2 |
| TC34953 | 379 | 2950 | 2267 | 5359 | 3465 | 5921 | −3.9 |
| TC24344 | 473 | 528 | 359 | 1189 | 1506 | 2141 | −3.7 |
| TC33957 | 4504 | 2776 | 5281 | 12197 | 14665 | 15262 | −3.6 |
| TC40061 | 4693 | 1355 | 4866 | 7669 | 10158 | 7310 | −3.5 |
| TC36858 | −65 | 113 | 276 | 904 | 449 | 854 | −3.3 |

TABLE 16-continued

Genes downregulated by aging in C57BL/6 mice gastrocnemius from Mu19K GeneChip

| Probe Set | oc1 | oc2 | oc3 | yc1 | yc2 | yc3 | Fold Change |
|---|---|---|---|---|---|---|---|
| TC15621 | 3342 | 3801 | 2088 | 5802 | 5651 | 7667 | −3.1 |
| TC22866 | 2973 | 2064 | 3961 | 6385 | 9965 | 9570 | −3.1 |
| TC36347 | 1077 | 2585 | 1662 | 4287 | 6166 | 4493 | −3.0 |
| TC26944 | 13744 | 8497 | 7171 | 26871 | 31183 | 24244 | −3.0 |
| TC36854 | −679 | 139 | −105 | 2255 | 4600 | 2220 | −2.9 |
| TC32868 | −194 | 501 | −963 | 1491 | 1485 | 569 | −2.9 |
| TC33934 | −2432 | 4016 | 2471 | 8604 | 6093 | 6420 | −2.9 |
| TC34857 | 819 | 360 | −165 | 2160 | 2933 | 3161 | −2.9 |
| TC37125 | 1946 | 486 | 1276 | 2675 | 2376 | 2256 | −2.7 |
| TC34321 | 1133 | 1989 | 1051 | 2901 | 3233 | 3270 | −2.6 |
| TC35099 | 1565 | 3225 | 2314 | 3774 | 5816 | 7280 | −2.6 |
| TC22794 | 420 | 153 | 343 | 1106 | 1654 | 1016 | −2.6 |
| TC28206 | −519 | −812 | −715 | 778 | 784 | 816 | −2.5 |
| TC17374 | 44879 | 40619 | 41419 | 95128 | 124767 | 111416 | −2.5 |
| TC19536 | 38 | 165 | 264 | 626 | 476 | 617 | −2.5 |
| TC39309 | 708 | 927 | 1767 | 2405 | 2161 | 1651 | −2.5 |
| TC14511 | 2772 | 859 | 1861 | 2932 | 4587 | 3089 | −2.4 |
| TC25977 | −125 | 907 | −393 | 1714 | 939 | 1724 | −2.4 |
| TC34555 | 713 | 2541 | 2642 | 3098 | 3608 | 4297 | −2.4 |
| TC40318 | 2484 | 2040 | 3012 | 5440 | 5650 | 5710 | −2.4 |
| TC22050 | 721 | 421 | 545 | 944 | 1092 | 1638 | −2.4 |
| TC23531 | 264 | 555 | 298 | 677 | 1076 | 612 | −2.4 |
| TC35434 | 1150 | 743 | 1300 | 2736 | 2496 | 1833 | −2.4 |
| TC37551 | −265 | 73 | −169 | 118 | 422 | 232 | −2.4 |
| TC34651 | 792 | 2193 | 2064 | 3432 | 3751 | 4517 | −2.3 |
| TC49365 | −286 | −312 | −315 | 176 | 172 | 252 | −2.3 |
| TC26535 | 4580 | 11925 | 9572 | 12361 | 20086 | 21438 | −2.2 |
| TC25372 | 12 | 141 | −161 | 348 | 276 | 386 | −2.2 |
| TC28752 | 816 | 1567 | 2442 | 3958 | 2783 | 2378 | −2.2 |
| TC21901 | 1491 | 754 | 1326 | 2284 | 2539 | 2382 | −2.2 |
| TC41250 | 628 | 279 | 660 | 782 | 1093 | 1096 | −2.2 |
| TC20836 | 102 | 182 | 514 | 781 | 452 | 820 | −2.2 |
| TC39607 | 1263 | 1289 | 765 | 1277 | 1861 | 1895 | −2.2 |
| TC33236 | 1991 | 2588 | 3851 | 5152 | 4945 | 5421 | −2.1 |
| TC41556 | 1138 | 1047 | 1367 | 2263 | 1972 | 1988 | −2.1 |
| TC41884 | 475 | 55 | 193 | 650 | 406 | 693 | −2.1 |
| TC31627 | 606 | 494 | 1343 | 1839 | 1123 | 2105 | −2.1 |
| TC35120 | 1298 | 1479 | 752 | 2993 | 2032 | 1705 | −2.1 |
| TC37978 | 664 | 425 | 875 | 1444 | 1620 | 1546 | −2.1 |
| TC32191 | 329 | 1419 | 700 | 2118 | 1560 | 2187 | −2.0 |
| TC39472 | 5773 | 5966 | 4650 | 9742 | 11750 | 11019 | −2.0 |
| TC36773 | 2894 | 3313 | 4085 | 5414 | 7595 | 6159 | −2.0 |
| TC38302 | 459 | 289 | 306 | 621 | 809 | 568 | −2.0 |
| TC28179 | 11576 | 8026 | 7030 | 16063 | 14643 | 19203 | −2.0 |

We claim:

1. The method of obtaining biomarkers of aging comprising the steps of:
   (a) comparing a gene expression profile of a multicellular organism subject's organ, tissue or cell; a gene expression profile from a chronologically older subject's organ, tissue or cell; and a gene expression profile from a calorically restricted subject's organ, tissue or cell, wherein the calorically restricted subject is the same chronological age as the chronologically older subject, and
   (b) identifying gene expression alterations that are observed when comparing the subject and the chronologically older subject and are not observed or are reduced in magnitude when comparing the subject and calorically restricted subject.

2. The method of claim 1 wherein one uses oligonucleotide arrays to compare the subjects' gene expression profile.

3. The method of claim 1 wherein the gene expression profile indicates a two-fold or greater increase or decrease in the expression of certain genes in chronologically aged subjects.

4. The method of claim 1 wherein the gene expression profile indicated a 3-fold or greater increase or decrease in the expression of certain genes in chronologically aged subjects.

5. The method of claim 1 wherein the gene expression profile indicates a 4-fold or greater increase or decrease in the expression of certain genes in chronologically aged subjects.

6. The method of claim 1 wherein the subject is a mammal.

7. The method of claim 6 wherein the mammal is selected from the group consisting of humans, mice and rats.

* * * * *

UNITED STATES PATENT AND TRADEMARK OFFICE
CERTIFICATE OF CORRECTION

PATENT NO. : 6,569,624 B1
DATED : May 27, 2003
INVENTOR(S) : Richard H. Weindruch et al.

It is certified that error appears in the above-identified patent and that said Letters Patent is hereby corrected as shown below:

Column 4,
Line 56, "2,15" should read -- 2, 15 --.

Column 7,
Line 54, "blofting" should read -- blotting --.
Lines 54-55, "2. Experimental Protocols" should be all on line 55.

Column 8,
Line 51, "(Na30)" should read -- (Na+) --.

Column 11,
Line 68, (Table 2), "-2,7" should read -- 2.7 --.

Column 19,
Line 21, (Table 5), "TI.225 (ubiquitin)" should read -- TI-255 (ubiquitin) --.

Column 20,
Lines 30 and 36, (Table 5), "Immune/inflammitory" should read
-- Immune/inflammatory --.

Column 23,
Line 58, (Table 7), "68" should read -- 87 --.

Column 24,
Line 5, (Table 6), "DNA metabolism" should read -- RNA metabolism --.
Line 21, (Table 6), "Stuctural" should read -- Structural --.
Line 55, (Table 7), "ot" should read -- of --.

Column 25,
Line 2, (Table 7), "ot" should read -- of --.
Line 13, (Table 7), "Dopaimne" should read -- Dopamine --.
Line 22, (Table 7), "106" should read -- 108 --.
Line 28, (Table 7), "Call" should read -- Ca++ --.
Line 44, (Table 7), "340" should read -- 140 --.
Line 45, (Table 7), "23" should read -- 73 --.
Line 47, (Table 7), "cotransponer" should read -- contransporter --.
Line 48, (Table 7), "actvator" should read -- activator --.

UNITED STATES PATENT AND TRADEMARK OFFICE
CERTIFICATE OF CORRECTION

PATENT NO. : 6,569,624 B1
DATED : May 27, 2003
INVENTOR(S) : Richard H. Weindruch et al.

It is certified that error appears in the above-identified patent and that said Letters Patent is hereby corrected as shown below:

Column 26,
Line 17, (Table 7), "Immune/inflammttory" should read -- Immune/inflammatory --.
Line 50, (Table 7), "Apaptotic" should read -- Apoptotic --.
Line 64, (Table 7), "Energey" should read -- Energy --.
Line 75, (Table 7), "Transtport" should read -- Transport --.

Column 27,
Line 69, (Table 8), "c-Knox" should read -- c-Krox --.

Column 28,
Line 2, (Table 7), "ot" should read -- of --.
Lines 47, 48 and 65, (Table 8), "Energey" should read -- Energy --.

Column 29,
Line 24, (Table 8), "37" should read -- 137 --.
Line 38, (Table 8), "AA02227" should read -- AA022127 --.
Line 56, (Table 8), "M80363" should read -- M80360 --.

Column 30,
Lines 36, 53 and 57, (Table 8), "Energey" should read -- Energy --.

Column 31,
Line 23, (Table 9), "glycopratetn" should read -- glycoprotein --.
Line 30, (Table 9), "Ig-gamna" should read -- Ig-gamma --.
Line 41, (Table 9), "G-proten-like" should read -- G-protein-like --.
Line 53, (Table 9), "Pennatal" should read -- Perinatal --.
Line 62, (Table 9), "syntnase" should read -- synthase --.

Column 32,
Line 16, (Table 9), "Neuratransmission" should read -- Neurotransmission --.

Column 33,
Line 5, (Table 9), "resistanc-asstd." should read -- resistance-asstd. --.
Line 21, (Table 9), "ctass" should read -- class --.
Line 25, (Table 9), "Els" should read -- Efs --.

Column 34,
Line 15, (Table 9), "Signal transdtuction" should read -- Signal transduction --.
Line 35, (Table 9), add -- from -- after "method" and before "which".

UNITED STATES PATENT AND TRADEMARK OFFICE
CERTIFICATE OF CORRECTION

PATENT NO.    : 6,569,624 B1
DATED         : May 27, 2003
INVENTOR(S)   : Richard H. Weindruch et al.

It is certified that error appears in the above-identified patent and that said Letters Patent is hereby corrected as shown below:

Column 35,
Line 25, (Table 10), "syntnase" should read -- synthase --.
Line 59, (Table 10), "C-" should read -- C++ --.

Column 36,
Line 73, (Table 10), "Exocytossis" should read -- Exocytosis --.

Column 38,
Line 11, (Table 10), "siganl" should read -- signal --.
Line 20, (Table 12), "1155" should read -- -1155 --.
Line 34, (Table 12), "TC46488" should read -- TC16488 --.
Line 36, (Table 12), "1738" should read -- -1738 --.
Line 37, (Table 12), "56" should read -- -56 --.
Line 38, (Table 12), "1070" should read -- -1070 --.
Line 54, (Table 12), "2800" should read -- -2800--.
Line 55, (Table 12), "117" should read -- -117 --.
Line 66, (Table 12), "47" should read -- -47 --.

Column 39,
Line 14, (Table 12), "470" should read -- -470 --.
Line 22, (Table 12), "TC36933" should read -- TC36033 --.
Line 25, (Table 12), "918" should read -- -918 --.

Column 40,
Line 65, (Table 13), "M117446" should read -- AA117446 --.

Column 41,
Line 17, (Table 13), "M152695" should read -- AA152595 --.
Line 18, (Table 13), "M014024" should read -- AA014024 --.
Line 22, (Table 13), "L20276 1761 1059 1201 260 600 829 3.0" should read
-- AA168633 585 654 733 167 253 246 3.1 --.
Line 23, (Table 13), "AA168633 585 654 733 167 253 246 3.1" should read
-- L20276 1761 1059 1201 260 600 829 3.0--.

UNITED STATES PATENT AND TRADEMARK OFFICE
CERTIFICATE OF CORRECTION

PATENT NO. : 6,569,624 B1
DATED : May 27, 2003
INVENTOR(S) : Richard H. Weindruch et al.

It is certified that error appears in the above-identified patent and that said Letters Patent is hereby corrected as shown below:

Column 42,
Line 8, (Table 14), "M029728" should read -- AA029728 --.
Line 18, (Table 14), "M068780" should read -- AA068780 --.
Line 19, (Table 14), "M072334" should read -- AA072334 --.
Line 20, (Table 14), "M060808" should read -- AA060808 --.
Line 24, (Table 14), "M003162" should read -- AA003162 --.
Line 28, (Table 14), "M107137" should read -- AA107137 --.

Column 43,
Line 61, (Table 16), "492" should read -- -492 --.

Signed and Sealed this

Twenty-third Day of March, 2004

JON W. DUDAS
*Acting Director of the United States Patent and Trademark Office*